United States Patent
Hirao et al.

(10) Patent No.: US 7,101,992 B1
(45) Date of Patent: Sep. 5, 2006

(54) NUCLEIC ACID BASE PAIR

(75) Inventors: Ichiro Hirao, Asaka (JP); Masahide Ishikawa, Wako (JP); Tsuyoshi Fujihara, Wako (JP); Shigeyuki Yokoyama, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 379 days.

(21) Appl. No.: 09/787,196

(22) PCT Filed: Jul. 14, 2000

(86) PCT No.: PCT/JP00/04720

§ 371 (c)(1),
(2), (4) Date: Apr. 26, 2001

(87) PCT Pub. No.: WO01/05801

PCT Pub. Date: Jan. 25, 2001

(30) Foreign Application Priority Data

Jul. 15, 1999 (JP) .......................... 11-201450
May 2, 2000 (JP) ...................... 2000-133519

(51) Int. Cl.
*C07H 21/00* (2006.01)
*C07H 19/16* (2006.01)
*C07H 19/048* (2006.01)

(52) U.S. Cl. .................. 536/25.3; 536/27.81; 536/22.1; 435/91.1

(58) Field of Classification Search ................ 536/25.3, 536/27.81, 22.1; 435/91.1
See application file for complete search history.

(56) References Cited

U.S. PATENT DOCUMENTS 5,126,439 A * 6/1992 Rappaport ................. 536/23.1

OTHER PUBLICATIONS

Tor et al. (Journal of the American Chemical Society (1993), 115, 4461–4467).*
Gundersen (Tetrahedron Letters (1994), 35(19), 3155–8) (Abstract Sent).*
Ishikawa et al. (Nucleic Acids Symposium Series (1999), No. 42, pp. 125–126.*
Tor et al., "Site–Specific Enzymatic Incorporation of an Unnatural Base, $N^5$–(6–Aminohexyl)isoguanosine, into RNA," Journal of the American Chemical Society, 115:4461–4467 (1993).
Morales et al. "Efficient replication between non–hydrogen–bonded nucleoside shape analogs," Nature Structural Biology 5:950–954 (1998).
Kim et al., "Oligoribonucleotides Containing 8–oxo–7, 8–Dihydroguanosine and 8–oxo–7, 8–Dihydro–2'–O–Methylguanosine: Synthesis and Base Pairing Properties," Bioorganic & Medicinal Chemistry Letters 8:939–944 (1998).

Singer et al., "Effect ot 3' flanking neighbors on kinetics of pairing of dCTP pr dTTP opposite $O^6$–methylguanine in a defined primed oligonucletode with *Escherichia coli* DNA polymerase I is used," Proc. Natl. Acad. Sci. USA 86:8271–8274 (1989).
Ishikawa et al., "Chemical synthesis of novel base pairs and their enzymatic incorporation into DNA," Nucleic Acids Symposium Series 42:125–126 (1999).
Kikugawa et al., "Platelet Aggregation Inhibitors. 2. Inhibitors. of Platelet Aggregation by 5'–, 2–, 6–, and 8–Substituted Adenosines," Journal of Medicinal Chemistry 15:387–390 (1972).
Robins et al., "The synthesis of 2–,6–, and 2,6–halogens substituted 9–(2,3,–tri–0–acetyl–β–D–ribofuranosyl)purines," Nucleic Acids Symposium Series 9:61–63 (1981).
Ishikawa et al.., "Synthesis of 3–(2–doexy–β–D–ribofuranosyl) pyridin–2–one and 2–amino–6–(N, N–dimethylamino)–9–(2–deoxy–β–D–ribofuranosyl) purine derivatives for an unnatural base pair", Tetrahedron Letters, vol. 41, No. 20 (May 21, 2000) pp. 3931–3934.
Solomon et al., "Chemical Synthesis and Characterization of Duplex DNA Containing a New Base Pair: A Nondisruptive, Benzofused Pyrimidine Analog", J. Org. Chem., vol. 58 (1993) pp. 2232–2243.
Voegel et al., "Nonstandard Hydrogen Bonding in Duplex Oligonucleotides. the Base Pair between an Acceptor–Donor–Donor Pyrimidine Analog and a Donor–Acceptor–Acceptor Purine Analog", J. Am. Chem. Soc., vol. 116 (1994) pp. 6929–6930.
Piccirilli et al., "Enzymatic incorporation of a new base pair into DNA and RNA extends the genetic alphabet", NATURE, vol. 343 (Jan. 4, 1990) pp. 33–37.
Huss et al. "Synthesis of Various Branched Triribonucleoside Diphosphates by Site–Specific Modification of a Diphenylcarbamoyl–Protected Guanine Residue", J. Org. Chem., vol. 53 (1988) p. 499–506.
Kool, Eric T., "Synthetically modified DNAs as substrates for polymerases", Current Opinion in Chemical Biology 4: 602–608, 2000.

* cited by examiner

*Primary Examiner*—James O. Wilson
*Assistant Examiner*—Michael C. Henry
(74) *Attorney, Agent, or Firm*—Jonh B. Alexander; Peter F. Corless; Palmer & Dodge LLP

(57) ABSTRACT

A novel artificial nucleic acid base pair which is obtained by forming a selective base pair by introducing a group having steric hindrance (preferably a group having steric hindrance and static repulsion and a stacking effect) and can be recognized by a polymerase such as DNA polymerase; a novel artificial gene; and a method of designing nucleic acid bases so as to form a selective base pair with the use of steric hindrance, static repulsion and stacking effect at the base moity of the nucleic acid. An artificial nucleic acid comprising these bases; a process for producing the same; a codon containing the same; a nucleic acid molecule containing the same; a process for producing a non-natural gene by using the same; a process for producing a novel protein by using the above nucleic acid molecule or non-natural gene, and the like.

4 Claims, 15 Drawing Sheets

SEQUENCE LISTING

<160> NUMBER OF SEQ ID NOS: 15

<210> SEQ ID NO 1
<211> LENGTH: 35
<212> TYPE: DNA
<213> ORGANISM: Artificial Sequence
<220> FEATURE:
<223> OTHER INFORMATION: Description of Artificial Sequence: Synthetic DNA template
<221> NAME/KEY: modified_base
<222> LOCATION: (7)
<223> OTHER INFORMATION: 2-amino-6-(N,N-dimethylamino)-9-(2'deoxy- B -D-ribofuranosyl) purine

<400> SEQUENCE: 1
tgctctntct tcctccctat agtgagtcgt attat      35

<210> SEQ ID NO 2
<211> LENGTH: 29

```
<212> TYPE: DNA
<213> ORGANISM: Artificial Sequence
<220> FEATURE:
<223> OTHER INFORMATION: Description of Artificial Sequence: Synthetic
      DNA template
<221> NAME/KEY: modified_base
<222> LOCATION: (5)
<223> OTHER INFORMATION: 2-amino-6-(N,N-dimethylamino)-9-(2'deoxy- B -D-
      ribofuranosyl) purine

<400> SEQUENCE: 2
agctntgtgt gtctccggta caactaggc                                    29

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA template
<221> NAME/KEY: modified_base
<222> LOCATION: (5)..(6)
<223> OTHER INFORMATION: 2-amino-6-(N,N-dimethylamino)-9-(2'deoxy- B -D-
      ribofuranosyl) purine

<400> SEQUENCE: 3
agctnngtgt gtctccggta caactaggc                                    29

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA template
<221> NAME/KEY: modified_base
<222> LOCATION: (5)
<223> OTHER INFORMATION: 2-amino-6-(N,N-dimethylamino)-9-(2'deoxy- B -D-
      ribofuranosyl) purine
<221> NAME/KEY: modified_base
<222> LOCATION: (7)
<223> OTHER INFORMATION: 2-amino-6-(N,N-dimethylamino)-9-(2'deoxy- B -D-
      ribofuranosyl) purine

<400> SEQUENCE: 4
agctntntgt gtctccggta caactaggc                                    29

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA template
<221> NAME/KEY: modified_base
<222> LOCATION: (5)
<223> OTHER INFORMATION: 2-amino-6-(N,N-dimethylamino)-9-(2'deoxy- B -D-
      ribofuranosyl) purine
<221> NAME/KEY: modified_base
<222> LOCATION: (8)
<223> OTHER INFORMATION: 2-amino-6-(N,N-dimethylamino)-9-(2'deoxy- B -D-
      ribofuranosyl) purine

<400> SEQUENCE: 5
agctntgngt gtctccggta caactaggc                                    29

<210> SEQ ID NO 6
<211> LENGTH: 29
<212> TYPE: DNA
<213> ORGANISM: Artificial Sequence
<220> FEATURE:
```

```
<223> OTHER INFORMATION: Description of Artificial Sequence: Synthetic
      DNA template
<221> NAME/KEY: modified_base
<222> LOCATION: (5)
<223> OTHER INFORMATION: 2-amino-6-(N,N-dimethylamino)-9-(2'deoxy- B -D-
      ribofuranosyl) purine
<221> NAME/KEY: modified_base
<222> LOCATION: (9)
<223> OTHER INFORMATION: 2-amino-6-(N,N-dimethylamino)-9-(2'deoxy- B -D-
      ribofuranosyl) purine

<400> SEQUENCE: 6
agctntgtnt gtctccggta caactaggc                                   29

<210> SEQ ID NO 7
<211> LENGTH: 35
<212> TYPE: DNA
<213> ORGANISM: Artificial Sequence
<220> FEATURE:
<223> OTHER INFORMATION: Description of Artificial Sequence: Synthetic
      DNA template

<400> SEQUENCE: 7
tgctctatct tcctccctat agtgagtcgt attat                            35

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: Synthetic
      DNA template

<400> SEQUENCE: 8
tgctctgtct tcctccctat agtgagtcgt attat                            35

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA template

<400> SEQUENCE: 9
agctgtgtgt gtctccggta caactaggc                                   29

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: synthetic
      coding strand

<400> SEQUENCE: 10
ataatacgac tcactatagg g                                           21

<210> SEQ ID NO 11
<211> LENGTH: 17
<212> TYPE: RNA
<213> ORGANISM: Artificial Sequence
<220> FEATURE:
<223> OTHER INFORMATION: Description of Artificial Sequence: Synthetic
      RNA oligonucleotide
<221> NAME/KEY: modified_base
<222> LOCATION: (11)
<223> OTHER INFORMATION: Variable nucleotide
```

-continued

```
<400> SEQUENCE: 11
gggaggaaga nagagca                                                  17

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
actcactata gggaggaaga                                               20

<210> SEQ ID NO 13
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cgactcacta taggg                                                    15

<210> SEQ ID NO 14
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ctatagggag gaga                                                     14

<210> SEQ ID NO 15
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gcctagttgt accg                                                     14
```

NUCLEIC ACID BASE PAIR

REFERENCE TO RELATED APPLICATIONS

This application is a 371 of PCT/JP00/04720 filed Jun. 14, 2000.

FIELD OF INVENTION

The present invention relates to formation of selective novel artificial nucleic acid base pair by utilizing steric hindrance.

The present invention further relates to replication and transcription of nucleic acid using the novel artificial nucleic acid base pair of the present invention, and a system for protein synthesis or functional nucleic acid. More particularly, the present invention pertains the novel artificial nucleic acid having properties to form selective base pair by applying steric hindrance, preferably to form selective base pair by applying steric hindrance, electrostatic repulsive force or stacking action, a process for production thereof, codon containing the same, nucleic acid molecule containing the same, a process for production of novel protein using the above nucleic acid molecules or non-natural gene.

BACKGROUND ART

Genetic information of organisms in the earth are transferred by using nucleic acids comprising of four bases consisting of adenine (A), guanine (G), cytosine (C) and thymine (T) as a gene. Proteins are synthesized according to genetic informations of mRNA which is transcribed from DNA of gene. In that occasion, 64 types of codon consisting of 3 bases ($4^3$=64) correspond to 20 types of amino acids.

If novel nucleic acid base (X and Y, in which X and Y form specific base pair) can be created in addition to already known for bases (A, G, C, T), numbers of codon can be increased greatly ($6^3$=216). As a result, proteins containing non-natural amino acids can possibly be synthesized by matching the newly created codons with non-natural amino acids [J. D. Bain, et al. Nature, 356, 537–539 (1992)].

Heretofore, a pair of isocytosine and isoguanine has been reported as an artificial base pair except for A-T and G-C. Isoguanine tends to form base pair with thymine due to tautomerism of isoguanine [C. Switzer, et al. J. Am. Chem. Soc. 111, 8322–8323 (1989); C. Y. Switzer, et al. Biochemistry 32, 10489–10496 (1993)]. Several novel base pairs have been reported, but there were problems on recognition by polymerase and no practical use has known [J. A. Piccirilli, et al., Nature, 343, 33–37 (1990); J. Horlacher, et al. Proc. Natl. Acad. Sci. USA, 92, 6329–6333 (1995); J. C. Morales, et al., Nature struct. biol., 5, 954–959 (1998)].

Nucleic acid molecules having various functions were found by in vitro selection method [A. D. Ellington, et al. Nature 346, 818–822 (1990); C. Tuerk, et al. Science 249, 505–510 (1990)]. If the novel base pair X-Y hereinabove can be recognized by polymerases such as DNA polymerase, RNA polymerase and reverse transcriptase, the present in vitro selection method using 4 bases can be performed by using 6 bases, then possibility to create nucleic acid molecules having novel function, which could not be practically realized by using 4 bases, can be expected.

Further, creation of novel base pair has expected for treatment of hereditary diseases caused by gene abnormality, in which one or more base in the gene is replaced by different base.

We have studied extensively to created novel artificial nucleic acid base pairs, which could not form base pair with natural nucleic acid, but could selectively form base pair by themselves and could be recognized by various polymerases. We have found that formation of nucleic acid base pair could be inhibited by applying steric hindrance of nucleic acid base, and formation of selective base pair between newly designed nucleic acid bases could be made. Further, we have found that such the newly designed nucleic acids could be recognized by various natural polymerases.

For example, in order not to form base pair with thymine but to form steric hindrance with keto group at position-6 of thymine, 2-amino-6-(N,N-dimethylamino)purine (hereinafter designates as X), in which two bulky methyl groups are introduced in amino group at position-6 of 2,6-diaminopurine, is designed. As a result, the X does not form base pair with thymine, but bases such as pyridine-2-one (hereinafter designates as Y), an analog of thymine, in which oxo group at position-6 is replaced by hydrogen atom, can form base pair with X (refer to FIG. 1).

Further, we have synthesized DNA oligomer containing 2-amino-6-(N,N-dimethylamino)-9-(2'-deoxy-β-D-ribofuranosyl)purine (hereinafter designates as dX) and 3-(2'-deoxy-5'-triphosphoro-β-D-ribofuranosyl)pyridine-2-one (hereinafter designates as dYTP), and found that dYTP or its ribonucleotide (rYTP) could be incorporated selectively into DNA or RNA as a complementary strand of the above dX.

This compound could hinder base pairing with natural base such as thymine (or uridine) (refer to FIG. 2b) and cytosine in some extent due to steric bulkiness of dimethylamino group in the base (dx in FIG. 2a). However, this steric hindrance could affect to the neighboring bases, and simultaneously could give inferior effect on stacking between bases, and resulted low rate of incorporation of dYTP by Klenow fragment as well as insufficient suppression for incorporation of thymidine triphosphate (dTTP) to dx.

We have examined novel artificial base pair by considering not only steric hindrance but also electrostatic repulsion between bases and stacking action with the neighboring bases, and could obtain artificial base pair with superior selectivity.

DISCLOSURE OF INVENTION

The present invention provides ideas for selective formation of novel artificial nucleic acid base pair as a result of recognition of base pairing by polymerase such as DNA polymerase by utilizing steric hindrance between base pairs, preferably be generating steric hindrance between only base pair plane without giving deterioration for stacking between bases and more preferably by selecting bases utilizing electrostatic repulsion against natural bases.

An aspect of the present invention is to provide novel artificial nucleic acid base pair which does not form base pair with natural nucleic acid and forms selective base pair in themselves as well as being recognized by various polymerases. Further aspect of the present invention is to provide artificial nucleic acid, codon containing the same, nucleic acid molecule, non-natural gene and application thereof.

The present invention relates to a method for constructing selective base pair comprising introducing a group having ability to form steric hindrance, preferably a group having ability to form steric hindrance and electrostatic repulsion, and stacking action in nucleic acid base. More particularly, the present invention relates to a method for constructing selective base pair wherein the said group having ability to form steric hindrance is a group to hinder formation of base pair with base part of natural nucleic acid, to hinder formation of base pair with base part of natural nucleic acid by an action of said steric hindrance and electrostatic repulsion, and to form stable structure with neighboring bases by the stacking action, and the said base pair can be recognized by polymerase.

Further, the present invention relates to a method for designing nucleic acid to construct selective base pair comprising utilizing steric hindrance in the nucleic acid base part, preferably utilizing steric hindrance and electrostatic repulsion, and stacking action in the nucleic acid base part. More particularly, the present invention relates to a method for designing nucleic acid to construct selective base pair comprising utilizing steric hindrance, preferably hindering to construct base pair with the natural nucleic acid base part by utilizing steric hindrance and electrostatic repulsion and stabilizing with the neighboring bases by the stacking action, and the said base pair can be recognized by polymerase.

The present invention relates to a nucleic acid, which can construct selective base pair, prepared by introducing a group having ability to form steric hindrance, preferably a group having ability to form steric hindrance and electrostatic repulsion, and stacking action in nucleic acid base. More particularly, the present invention relates to a nucleic acid for constructing selective base pair wherein the said group having ability to form steric hindrance, preferably having ability to form steric hindrance and electrostatic repulsion is to hinder formation of base pair with base part of natural nucleic acid, and more preferably to stabilize with the neighboring bases by the stacking action, and the said base pair can be recognized by polymerase.

The present invention discloses novel artificial nucleic acid which have similar behavior with nucleic acids containing natural bases and a method for designing such the nucleic acid. The nucleic acid of the present invention can be applied in the similar manner as the natural nucleic acid.

Consequently, the present invention relates to various applications using the nucleic acid of the present invention or nucleic acid designed by the method of the present invention.

More particularly, the present invention relates to a codon comprising one or more nucleic acid designed by the nucleic acid of the present invention or nucleic acid designed by the method of the present invention. The said codon can encode amino acids in the similar manner as the natural nucleic acid. The said amino acids can be non-natural amino acids. Further, the present invention relates to a nucleic acid molecule containing the nucleic acid of the present invention, the nucleic acid designed by the method of the present invention or the nucleic acid of the natural origin. The said nucleic acid molecule can encode proteins in the similar manner as the natural nucleic acid.

Further the said nucleic acid molecule can maintain whole or part of genetic informations of the natural gene. Nucleic acid having complementary strand can be prepared by an action of various polymerases on such the nucleic acid molecule. The present invention also relates to such the process for production of complementary strands.

In addition, the nucleic acid of the present invention or the nucleic acid designed by the method of the present invention can be introduced or substituted to a part of natural gene. Consequently, the present invention relates to a process for production of non-natural gene comprising introducing or substituting one or more nucleic acid of the present invention or the nucleic acid designed by the method of the present invention into the natural gene. The introduction or substitution can be performed with the codon unit of the present invention as described hereinbefore.

Further, the present invention relates to a process for production of protein having amino acid sequence based on codons of the non-natural gene or the nucleic acid of the present invention. Protein to which non-natural amino acid is introduced or substituted in the part of natural protein can be produced in case that codon containing the nucleic acid of the present invention or the nucleic acid designed by the method of the present invention encodes non-natural amino acid.

Consequently, the present invention provides a process for production of novel protein comprising substituting or introducing other natural or non-natural amino acid, preferably non-natural amino acid in a part of natural protein by the method of the present invention. According to this method, functions of amino acids in the protein coded by natural gene can be screened. The present invention also relates to a method for screening function of each amino acid of protein encoded by natural gene.

The present invention also relates to a microorganism transformed by non-natural gene containing the nucleic acid of the present invention or nucleic acid designed by the method of the present invention (hereinafter simply designates as the nucleic acid of the present invention).

Further, since the novel base pair of the present invention does not constitute base pairing with the natural bases, it is useful for treatment of hereditary diseases caused by gene in which one or more base is replaced by other base. The present invention provides pharmaceutical composition comprising novel base pair or a base in the said base pair.

An object of the present invention is to provide artificial nucleic acid which does not form base pair with a base of the natural nucleic acid and can be recognized by polymerase. The conventional artificial nucleic acid has produced by attempting to change at the position of hydrogen bond, as a result, base pairing with a base of the natural nucleic acid could not be hindered substantially as well as showing insufficient base pair selectivity. We have solved such the problem by introducing a group forming the steric hindrance, preferably by introducing a group forming steric hindrance and electrostatic repulsion and having stacking action. The present invention provides novel artificial nucleic acid which can form selective base pairing with artificial nucleic acids themselves.

Consequently, the present invention wilt be explained more concretely by referring examples hereinbelow, but these examples are illustrated only for the purpose of better understanding of the present invention, and the fact that the present invention is not limited by these examples is obvious according to the technical idea of the present invention explained hereinbefore.

A group which forms steric hindrance in the base part of the nucleic acid of the present invention can be a group only hinder hydrogen bonding with deteriorated base, and is not limited if it does not deteriorate for the properties as a base of nucleic acid. Preferably, the size thereof may be not to hinder formation of base pairs of other bases in the nucleic acid sequence. In addition, it is preferable not to have polar group and activated hydrogen atom, but is not necessary to consider if these polar group and activated hydrogen atom are located in the positions having distance impossible to form hydrogen bonding Examples of group which forms steric hindrance are, for example, lower alkyl group such as ethyl, isopropyl, isobutyl or t-butyl group, preferably branched lower alkyl group, lower alkoxy group consisting of methyl or these lower alkyl groups, di-lower alkylamino group substituted by methyl or these lower alkyl groups and silyl group substituted by methyl or these lower alkyl groups.

Conventional chemical synthesis can be applied for methods of introducing groups to form steric hindrance in the base.

Examples of groups having actions for steric hindrance, electrostatic repulsion and stacking action on base part of the nucleic acid are group having steric hindrance which hinders hydrogen bonding having deteriorated action between bases, having electrostatic repulsive force and having π electron for stacking action. These groups are not limited if they have deteriorating actions as a nucleic acid base. More preferably, a group having size not to hinder base pairing for other nucleic acid is preferable. Further, groups without having polar site for hydrogen bond and activated hydrogen atom are preferable, however if these polar site or activated hydrogen is located at distal position where hydrogen bonding may be impossible, it may not necessary to consider.

Examples of groups having steric hindrance, electrostatic repulsion and stacking action in the base pair of the present invention are preferably aromatic heterocyclic group having planar structure. Such aromatic heterocyclic group has sufficient size for steric hindrance on the planar direction of molecule, and can generate electrostatic repulsion by different atoms, and also is expected to show stacking action by π electron of aromatic heterocyclic group.

Examples of such the aromatic heterocyclic group are, concretely, five membered or six membered aromatic heterocyclic group having one or two sulfur atom, oxygen atom or nitrogen atom. These aromatic heterocyclic groups can be condensed-ring, polycyclic or monocyclic group. Among them, monocyclic group is preferable due to steric size. These aromatic heterocyclic groups can have any substituents, but a group without having large substituent is preferable due to possibility to cause stereospecific limitation or generation of deteriorative hydrogen bonding. Examples of substituents are hydroxyl, amino, carbonyl, lower alkyl of carbon 1–5, lower alkoxy, lower alkylamino or nitro.

Conventional chemical synthesis can be applied for methods of introducing groups to form steric hindrance, electrostatic repulsion or stacking action in the base.

Nucleic acid of the present invention is artificial nucleic acid which can be recognized by polymerase. Examples of polymerase can be any polymerase, preferably DNA polymerase and RNA polymerase. Recent studies on structural analysis of polymerase indicates that interaction of polymerase and nucleic acid is essentially identical with each other. Formation of base pair of the present invention relates to essential nature of polymerase, consequently, the base pair formation of the present invention can be utilized not only for DNA polymerase and RNA polymerase but also for all polymerase including reverse transcriptase.

Further, configuration of nucleic acid can be calculated by analysis of molecular configuration or precise determination of distance between atoms. Consequently, by applying these results, chemical structure, which causes steric hindrance in one side and provides one or more hydrogen bonds, preferably two hydrogen bonds in other side, can be designed. Consequently, the present invention includes a method for designing artificial nucleic acid based on steric hindrance of the nucleic acid, preferably steric hindrance in the base part of nucleic acid, preferably in addition thereto, electrostatic repulsion and stacking action. In the designing base pair of the present invention, designing based on Watson-Crick type base pair is conventional, but Hoogsteen base pairing may also be applicable.

Nucleic acid of the present invention can be a nucleic acid designed by steric hindrance of nucleic acid, preferably designed by steric hindrance in the base part of the nucleic acid, and is preferable to form selective base pairing with each of artificial nucleic acid. Preferably, base pairing of artificial nucleic acid can be recognized by polymerase and more preferably the complementary strand can be constructed similar to the natural nucleic acid by and action of polymerase.

Nucleic acid of the present invention can be synthesized by conventional chemical synthesis but is not limited to that method. Chemical synthesis is exemplified in FIG. 3, FIG. 4 and FIG. 5.

Method for incorporating nucleic acid of the present invention into the nucleic acid sequence can be performed by applying conventional method for incorporation of natural nucleic acid or by applying similar method thereof. For example, a method using DNA synthesizer, method for using polymerase and point mutation technology can be mentioned. Labeling can also be possible made as same as in the natural nucleic acid.

The present invention also includes nucleic acid which can be used for gene fragment or probe, and include nucleic acid molecule containing the nucleic acid of the present invention. The nucleic acid molecule of the present invention contains one or more nucleic acid of the present invention, and can be a single strand or double strands. Non-natural gene of the present invention includes natural gene in which whole of part of it is replaced by nucleic acid of the present invention, natural gene to which one or more nucleic acid of the present invention is added, or combination thereof. Such the non-natural gene of the present invention can be modified by the same or similar method used for the conventional modification of natural gene.

Consequently, nucleic acid molecule or non-natural gene of the present invention can be used for transformation of microorganisms by the same way as in the conventional natural gene by inserting suitable vector or phage and inserted into microorganisms to produce transformant containing the artificial nucleic acid of the present invention.

Further, new codon containing nucleic acid of the present invention can be designed. For example, the present novel artificial nucleic acid base is set as X and Y, combination thereof such as XXY, XYX, YXX, a combination by themselves, and AXA, TYT, CGX, ATX, which are combination of base of natural nucleic acid and artificial base of the present invention. Such codons can be designed. New codons can code natural amino acid, or non-natural amino acid. Further, functions such as transcription, transfer can be coded. Accordingly, the present invention not only provide novel artificial nucleic acid, but also providing possibility of designing completely new genetic code by designing new codon containing nucleic acid of the present invention. As a result of designing t-RNA corresponding to new codon of the present invention. New protein synthesis system can be designed by which large number of amino acid can be utilized. Usable amino acid can be amino acid utilized on protein synthesis on liposome. Consequently, the present invention provides novel protein synthetic system using codon of the present invention.

Heretofore, some amino acids in the natural protein are very difficult to substitute non-natural amino acid, or insertion of non-natural amino acid into the natural protein is also very difficult. According to the protein synthesis system of the present invention, proteins containing desired non-natural amino acid can be produced by substituting or inserting the nucleic acid having codon of desired position into the nucleic acid of the present invention. And such the conversion of amino acid resulted to make screening functions of amino acid in the protein.

BRIEF DESCRIPTION OF DRAWINGS

FIG. 10 Electrophoresis of RNA generated by transcription of T7 RNA polymerase using various rNTPs and template 1–3 and [α$^{32}$P]ATP.

BEST MODE FOR CARRYING OUT THE INVENTION

The present invention will be explained by the following examples in detail.

One of artificial base, 2,6-diaminopurine, could form base pairing with thymine by hydrogen bonding at position-6 of thymine. In order not to form base pairing 2,6-diaminopurine with thymine, two bulky methyl groups were introduced into the amino group at position-6 of 2,6-diaminopurine for colliding with this group and keto group of thymine at position-6 by steric hindrance, and synthesized to design 2-amino-6-(N,N-dimethylamino)purine (hereinafter a base of which is designated as X) of the formulae:

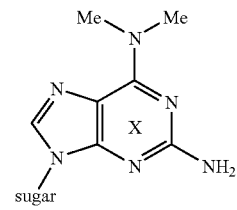

Figure 1:
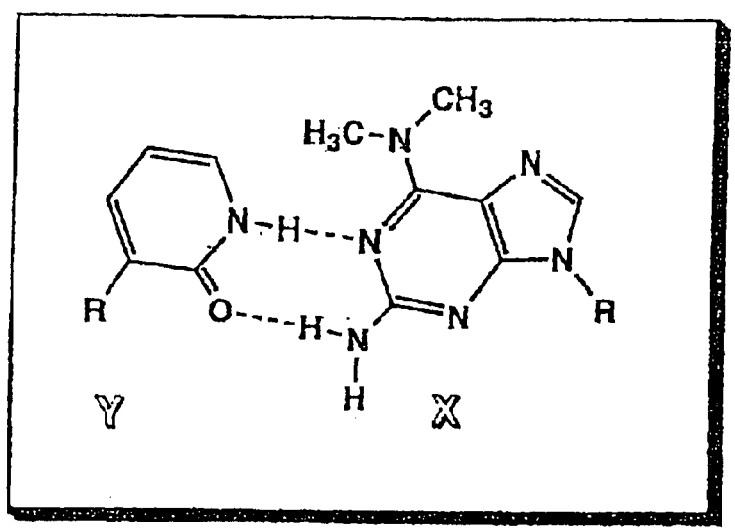
FIG. 1 shows novel artificial nucleic acid base pair (X-Y) by utilizing steric hindrance of the present invention. R in FIG. 1 indicates 2-deoxy-β-D-ribofuranosyl.
Figure 1:
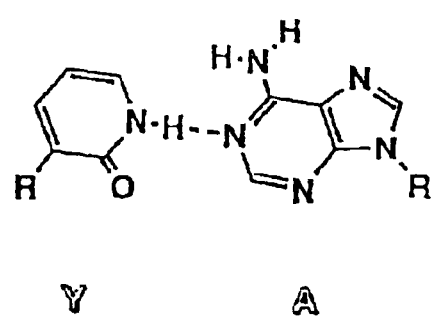
Figure 1:
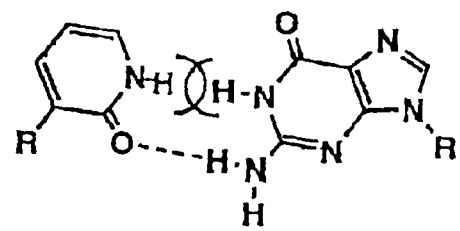
Figure 1:
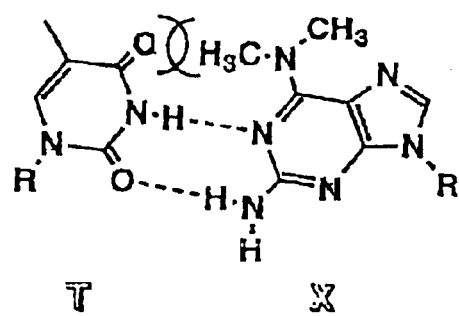
Figure 1:
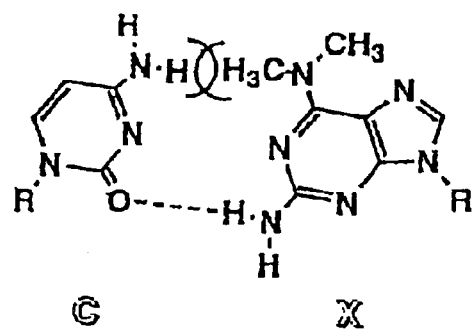

Accordingly, X could not form base pairing with thymine an analogous base in which oxo group at position-6 of thymine is replaced by hydrogen, pyridine-2-one (hereinafter the base of which is designated as Y) could for base pairing with X (refer to FIG. 1). Lower part of FIG. 1 illustrates binding not to form base pairing these bases X and Y with other bases.

In order to examine formation of selective novel nucleic acid base pair by utilizing steric hindrance in the base pair X-Y, primer extension method of DNA and transcriptional reaction synthesizing RNA from DNA were applied. The primer extension method includes annealing template DNA oligomer with a primer oligomer, and adding DNA polymerase and 2'-deoxynucleotide-5'-triphosphate (dNTP) to extend complementary sequence of the template at 3'-terminal of the primer. Klenow fragment, which is deleted 5'-exonuclease from DNA polymerase I, one of DNA polymerase originated from *E. coli*, and T7 RNA polymerase, RNA polymerase originated from T7 phage, were herein used. Both enzymes are commonly used at present.

In order to incorporate X into the template DNA, amidite reagent of dX was synthesized. Also template DNA containing dX having base sequences hereinbelow (Template 3, 5, 6, 7, 8 and 9) and template DNA (Template 1, 2 and 4) and their primer (Primer 1, 2 and 3) for use of control experiments were synthesized.

Template DNA containing dX (Template 3, 5, 6, 7, 8 and 9):

Template 3: (SEQ ID NO: 1) dtgctctxtcttcctccctatagt-gagtcgtattat

Template 5: (SEQ ID NO: 2) dagctxtgtgtgtctccggtacaac-taggc

Template 6: (SEQ ID NO: 3) dagctxxgtgtgtctccggtacaac-taggc

Template 7: (SEQ ID NO: 4) dagctxtxtgtgtctccggtacaac-taggc

Template 8: (SEQ ID NO: 5) dagctxtgxgtgtctccggtacaac-taggc

Template 9: (SEQ ID NO: 6) dagctxtgtxtgtctccggtacaac-taggc

Template for using control experiment (Template 1, 2 and 4)

Template 1: (SEQ ID NO: 7) dtgctctatcttcctccctatagt-gagtcgtattat

Template 2: (SEQ ID NO: 8) dtgctctgtcttcctccctatagt-gagtcgtattat

Template 3: (SEQ ID NO: 9) dagctgtgtgtgtctccggtacaac-taggc

Primer (Primer 1, 2 and 3)

Figure 4:
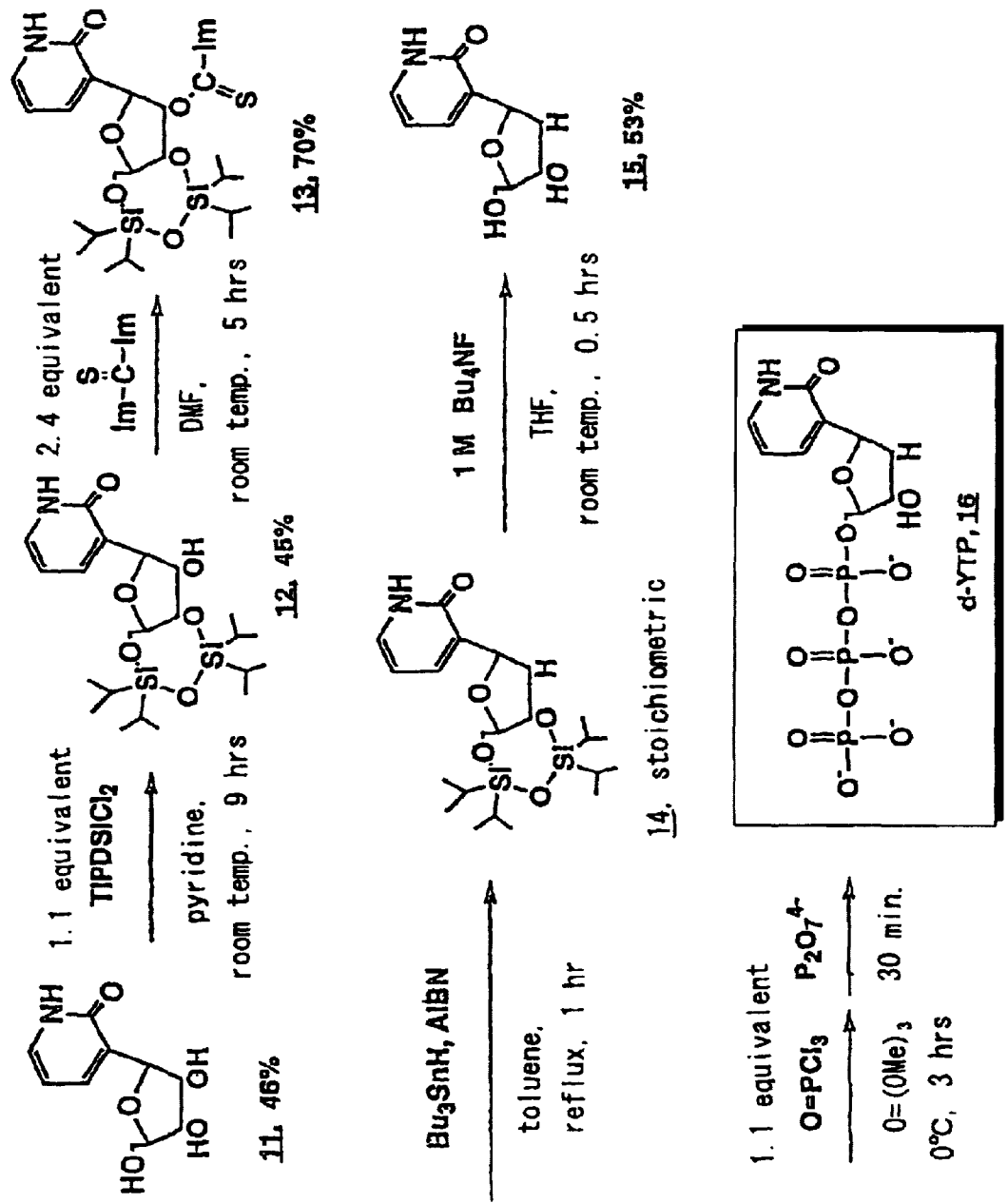
FIG. 4 shows synthetic scheme of dYTP of nucleic acid having base Y of the present invention.

Primer (Primer 1, 2 and 3)
  Primer 1 (SEQ ID NO: 13): dcgactcactataggg
  Primer 2 (SEQ ID NO: 14): dctatagggaggaga
  Primer 3 (SEQ ID NO: 15): dgcctagttgtaccg Substrates, dYTP and rYTP, were also synthesized (refer to FIG. 4)

5'-terminal of the primer was labeled with $^{32}$P using T4 polynucleotide kinase and [α-$^{32}$P]ATP. Primer labeled with $^{32}$P (0.5 µM) and template 1 and 3 (1 µM) and various dNTP (150 µM), wherein N means base, were used for primer extension by Klenow fragment (0.2 unit/µl) at 17° C. for 30 minutes.

A combination of primer and template used in the experiment is shown hereinbelow.

Figure 6:
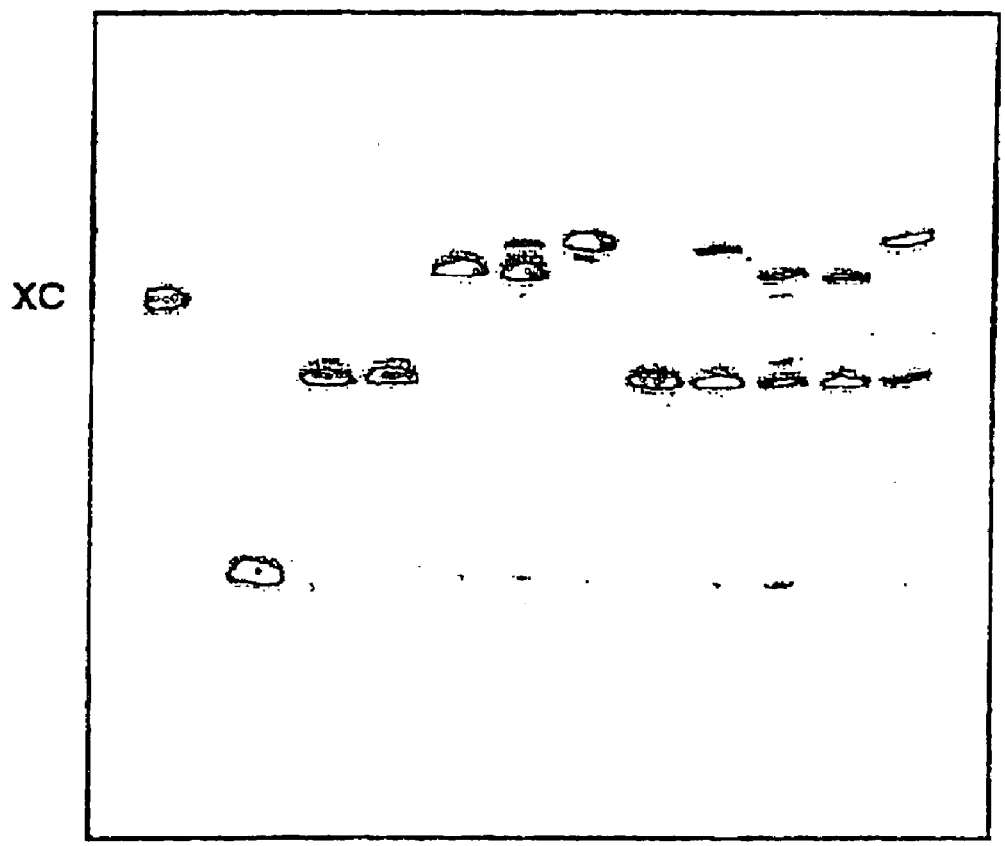
FIG. 6 shows 20% polyacrylamide 7M urea gel electrophoresis of primer extension reaction by Klenow fragment using 5'-terminal $^{32}$p labeled primer 1 (0.5 μM) and template 1, 3 (1 μM) and various dNTP (150 μM). Reaction was performed at 17° C. for 30 minutes. B is a graph of the result.

A case using template 1:
  Primer 1 (SEQ ID NO: 13):
    5'-$^{32}$pCGACTCACTATAGGG
  Template 1 (SEQ ID NO: 2):
    3'-TATTATGCTGAGTGATATCCCTCCTTCTATC TCGT A case using template 3:
  Primer 1 (SEQ ID NO: 13):
    5'-$^{32}$pCGACTCACTATAGGG
  Template 3: (SEQ ID NO: 1):
    3'-TATTATGCTGAGTGATATCCCTCCTTCTXTCT CGT The thus obtained product was electrophoresed using 20% polyacrylamide 7M urea gel and analyzed by using imaging plate (Phosphoroimager analysis). Result is shown in FIG. 6. In FIG. 6, left five, i.e. AG, AGC, AGT, AGY and AGCT, indicates cases using template 1, and right five indicates cases using template 3. Results indicate that a base y was incorporated into complementary strands of A, G and X. To the complementary strand X was incorporated also C and T in addition to Y (refer to FIG. 6).

For quantitative analysis of the incorporation, same experiments were conducted by adding only dNTP (150 µM) using primer 2 (1 µM) labeled with p32 at 5'-terminal and template 1, 2 and 3 (2 µM).

Primer and template used in the experiments are shown below.

Figure 7:
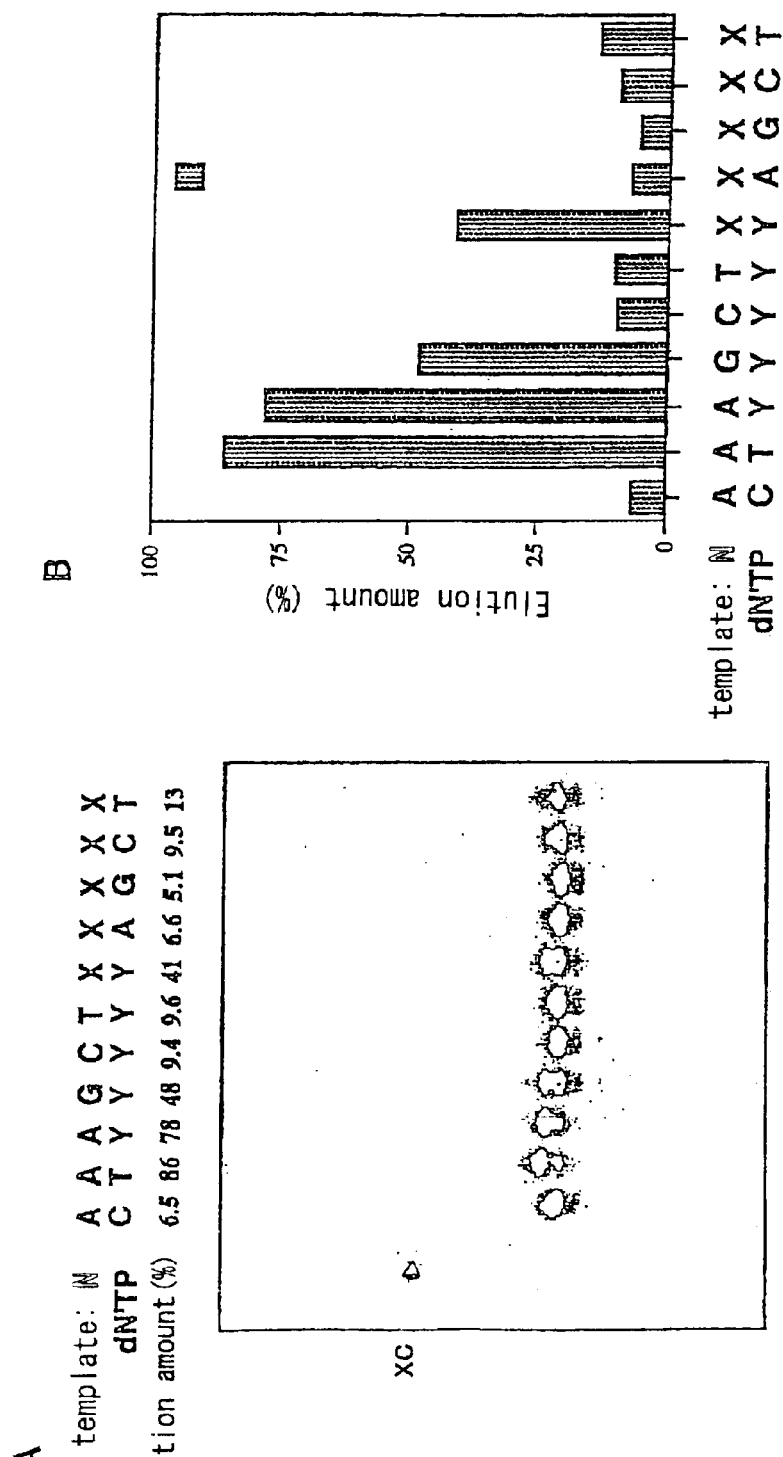
FIG. 7 shows 20% polyacrylamide 7M urea gel electrophoresis of single nucleotide insertion reaction by Klenow fragment using 5'-terminal $^{32}$p labeled primer 2 (1 μM) and template 1, 2, 3 (2 μM) and various dNTP (150 μM). Reaction was performed at 17° C. for 30 minutes. A is electrophoretic pattern with 29% polyacrylamide 7M urea electrophoresis and B is a graph of the result.

A case using template 1:
Primer 2 (SEQ ID NO: 14): 5'-$^{32}$pCTATAGGGAGGAGA
  Template 1: (SEQ ID NO: 7)
    3'-TATTATGCTGAGTGATATCCCTCCTTCTATC TCGT A case using template 2:
Primer 2 (SEQ ID NO: 14): 5'-$^{32}$pCTATAGGGAGGAGA
  Template 2: (SEQ ID NO: 8)
    3'-TATTATGCTGAGTGATATCCCTCCTTCTGTT CTGT A case using template 3:
Primer 2 (SEQ ID NO: 14): 5'-$^{32}$pCTATAGGGAGGAGA
  Template 3: (SEQ ID NO: 1)
    3'-TATTATGCTGAGTGATATCCCTCCTTCTXTC TCGT Results are shown in FIG. 7A and B. As a result, Y was incorporated into complementary strands of A, G and X at 78%, 48% and 41%, respectively, and Y, C and T were incorporated into complementary strand of X, at 41%, 9.5% and 13%, respectively. (Refer to FIG. 7)

Since Y was incorporated independently into not only X but also A and G, the following experiments were conducted in order to find out to what strands Y was incorporated when T and C were coexisted.

Primer 2 without labeling and template 2 were annealed, and [α-$^{32}$P]TTP and various amounts of dYTP were added thereto to find out ratio of inhibition of incorporation of [α-$^{32}$P]TTP into X by dYTP was investigated. Simultaneously with addition of DATP, effect of the said inhibition on incorporation of A into complementary strand of T next to X was investigated (refer to FIG. 8 A). As a result, when dYTP was added almost equivalent level of [α-$^{32}$P]TTP, incorporation of [α-$^{32}$P]TTP into X was inhibited at 50%. Same experiments were conducted by using template 1 and 2 for A and G. dYTP did not inhibit incorporation of [α-$^{32}$P]TTP into the complementary strand of A and the incorporation of [α-$^{32}$P]CTP into the complementary strand of G. (Refer to FIG. 8B for template 1 and C for template 2). Consequently, incorporation of dYTP into A and G was suppressed by coexisting TTP and dCTP.

In order to search effect of incorporation of Y, C and T into the complementary strand of X, when two X are presented on the template, $^{32}$P labeled primer 3 at 5'-terminal and template 4, 5, 6, 7, 8 and 9 were used for primer extension method. As a result, when two X were continued on the template, polymerase reaction was terminated at the position where two continuous X were existed whenever using any bases. In only the case where another base was incorporated between two X, only Y was incorporated into the complementary strand of the second X in the two X and continued synthesis of complementary strand (refer to FIG. 9).

Similarly, a transcription reaction by RNA polymerase using DNA containing X as template was examined. Using template 1–3, promoter region on this strand was duplicated, and the transcription reaction was examined using T7 RNA polymerase by adding [α$^{32}$P]ATP.

A combination of primer region and template used in this experiment is shown as follows.

A case using template 1–3
  Coding strand (SEQ ID NO: 10):
    5'-ATAATACGACTCACTATAGGG
  Template 1–3 (SEQ ID NO: 1, 7 or 8):
    3'-TATTATGCTGAGTGATATCCCTCCTTCTNTC TCGT
  (template 1: N=A
  template 2: N=G
  template 3: N=X)

Figure 10:
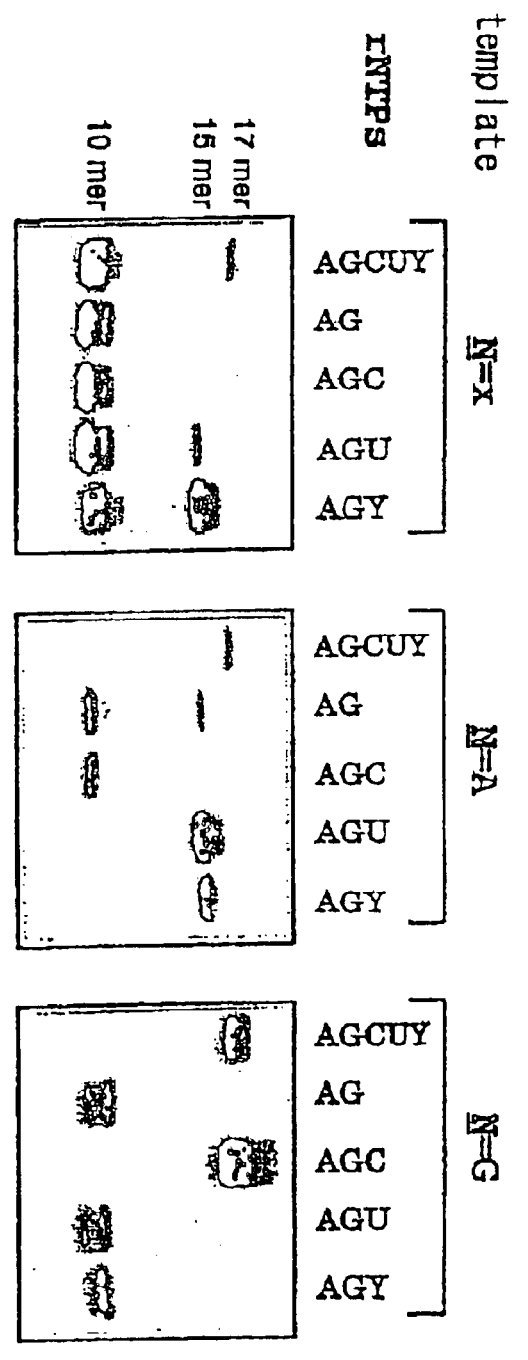

Result is shown in FIG. 10. In case of using template 3 (N=X), a band corresponding to a product as a result of selective incorporation of Y to X is observed. Trace amount of U was incorporated. In the case of template 1 (N=A), not only U but also Y was found to incorporated into the complementary strand of A. In the case of the template 2 (N=G), only C was incorporated, and almost no production as a result of incorporation of Y was observed.

Transcription reaction in the presence of rNTP was conducted. Using the template 1 (N=A) and the template 3

(N=X), the same as in the previous experiments, the transcription reaction was examined using T7 RNA polymerase by adding [α-$^{32}$P]ATP under the condition of rATP 2 mM, rGTP 2 mM, rCTP 2 mM, UTP 2 mM, and rYTP 1 mM, then generated full length of RNA was digested completely by RNase T2, nucleotide labeled at 3'-terminal was analyzed by 2-dimention TLC. Outline of this experiment is shown as follows.

coding strand; (SEQ ID NO: 10)

5'-ATAATACGACTCACTATAGGG template (SEQ ID NO: 1 or 8)

3'-TATTATGCTGAGTGATATCCCTCCTTCTNTCTCGT

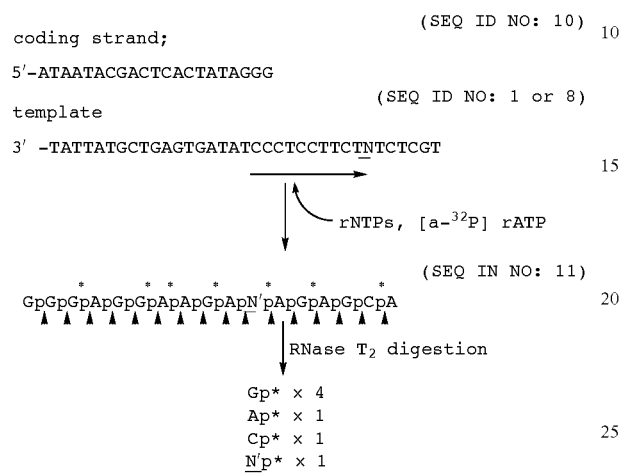

(SEQ IN NO: 11)

GpGpGpApGpGpApApGpApN'pApGpApGpCpA

RNase T₂ digestion

Gp* × 4
Ap* × 1
Cp* × 1
N'p* × 1

Figure 11:
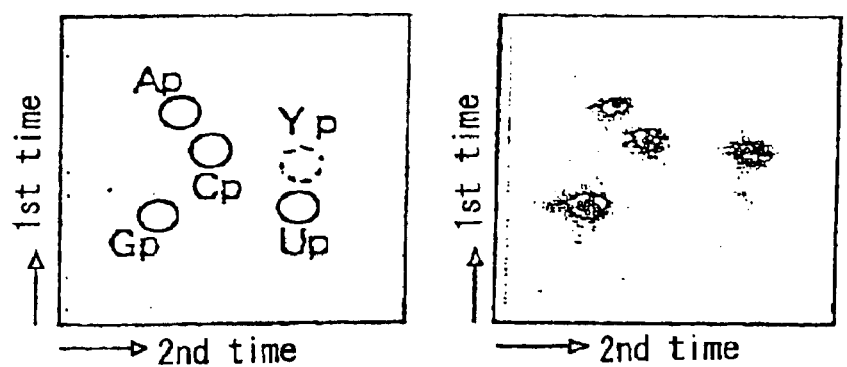
FIG. 11: Transcription was performed similar to the case in FIG. 10 with rNTP and generated RNA was purified by electrophoresis and digested by RNase T2. Resulted product was analyzed by 2-dimension TLC.
Figure 11:
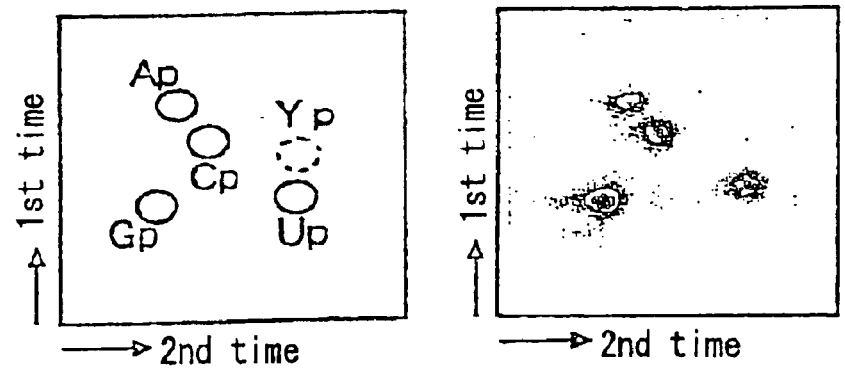

Results are shown in FIG. 11. In FIG. 11, spots encircled are indicated as spots observed by UV. In FIG. 11, A indicates the case of template 3 (N=X) and B in FIG. 11 indicates the case of template 1 (N=A). Theoretical values and experimental values in each case are shown in Table 1 as follows.

TABLE 1

Theoretical and measured values of the base for each template

| | Template 3 (N = X) | | Template 1 (N = A) | |
|---|---|---|---|---|
| Base | Theoretical Value | Measured Value | Theoretical Value | Measured Value |
| Gp | 4 | 4 | 4 | 4 |
| Ap | 1 | 1.05 | 1 | 0.92 |
| Cp | 1 | 0.94 | 1 | 0.78 |
| Up | 0 | 0.08 | 1 | 0.98 |
| Yp | 1 | 0.82 | 0 | 0.04 |

Result indicates that Y is almost selectively incorporated in case of transcription reaction using the template 3 (N=X) and trace amount of U is detected. In the case of template 1 (N=A), no incorporation of Y is observed.

Figure 2:
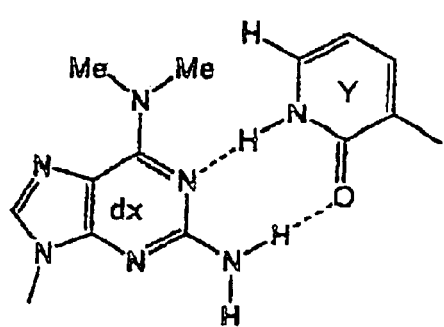
FIG. 2 shows novel artificial nucleic acid base pair (X2-Y) by utilizing base pairing caused by steric hindrance (FIG. 2a and b) and steric hindrance, electrostatic repulsion and stacking action.
Figure 2:
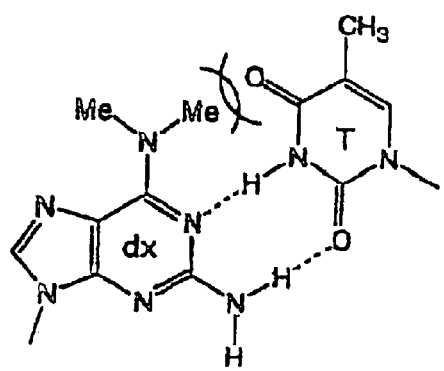
Figure 2:
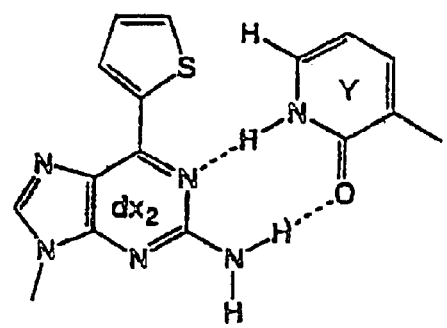
Figure 2:
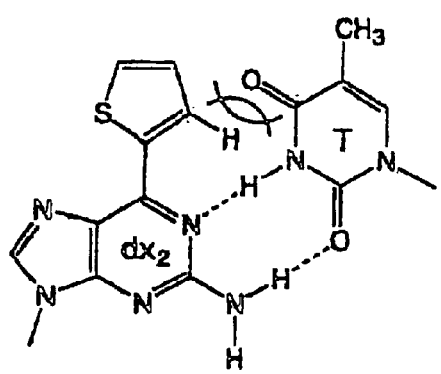
Figure 2:
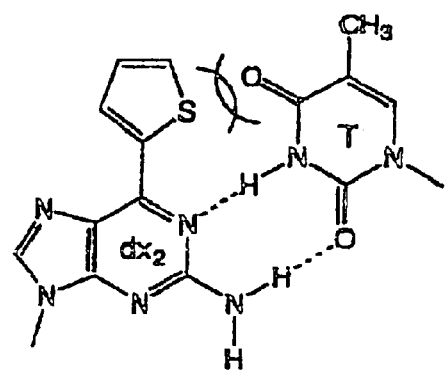
Figure 2:
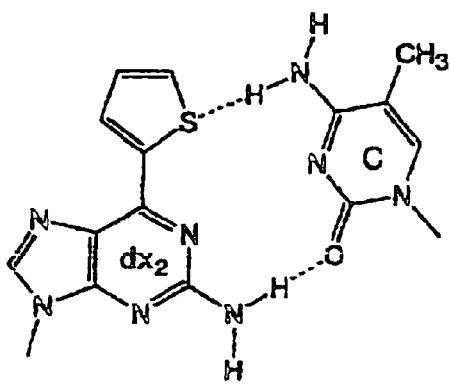

As explained hereinabove, the base X designed as such does not form base pairing with thymine, but the base such as analogous pyridine-2-one (base X) in which oxo at position-6 of thymine is replaced by hydrogen is able to form base pair with X (refer to FIG. 2a and b). Consequently, formation of selective nucleic base pair of X-Y has detected.

Although formation of base pair of natural base thymine (or uridine) (refer to FIG. 2b) could be excluded, simultaneously low rate of incorporation of dYTP by Klenow fragment was observed due to disadvantageous effect on stacking between bases as well as insufficient suppression of incorporation of thymidine triphosphate (dTTP) to dx.

Consequently, attempts were performed to incorporate aromatic substituents, which have no deteriorating effect on stacking between bases, to position-6 in dx as the replacement of dimethylamino group.

In the experiments, an example of incorporation of thiophene at position-6 is illustrated as follows.

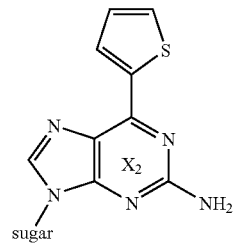

2-amino-6-(2-thienyl)-9-(2-deoxy-β-D-ribofuranosyl) purine [dx 2: the new base of which is designated as X2, and the previously synthesized 2-amino-6-(N,N-dimethylamino)-9-(2-deoxy-β-D-ribofuranosyl)purine is designated as dx] was synthesized. Incorporation of dYTP and rYTP for templates including this base was examined.

Figure 5:
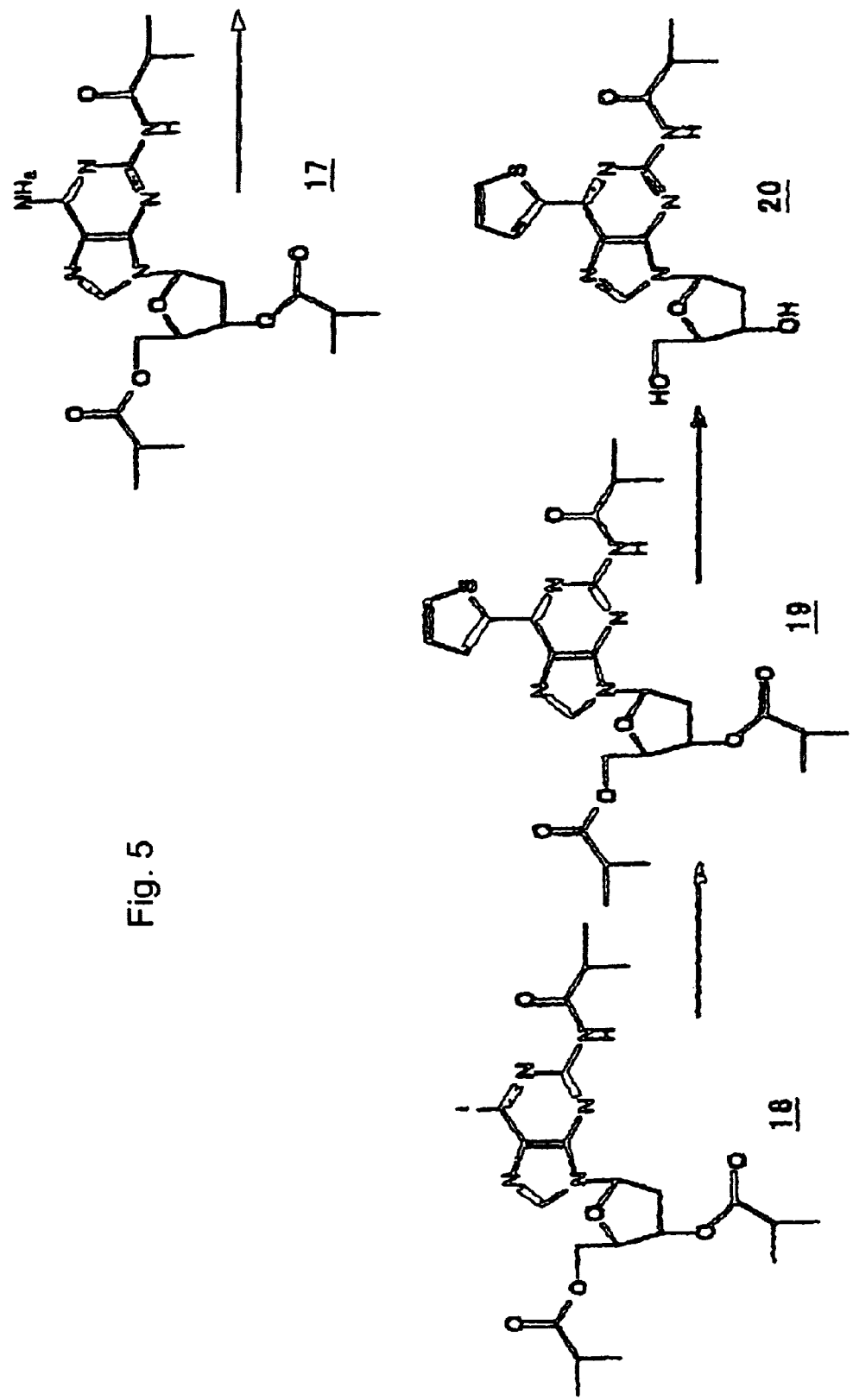
FIG. 5 shows synthetic scheme of amidite reagent of dx2 of nucleic acid having base X2 of the present invention.
Figure 5:
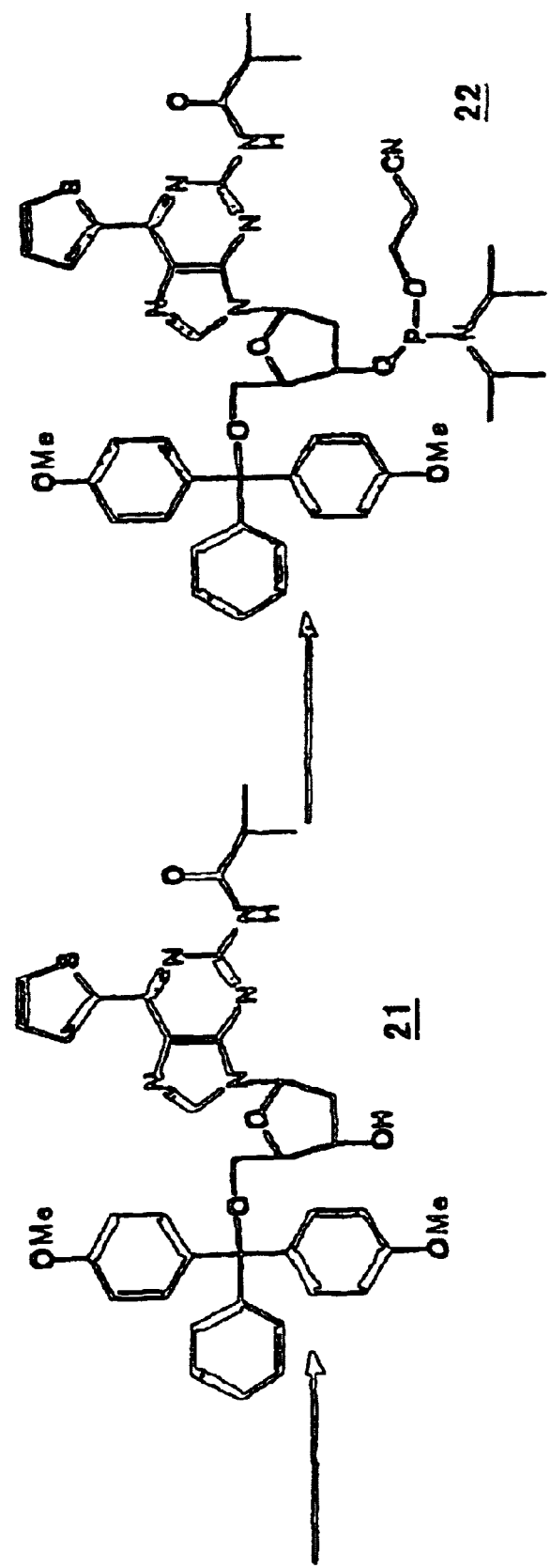

Outline of preparation of amidite reagent for dx for synthesis of template DNA is illustrated in FIG. 5. In detail, refer to example 2. This amidite reagent could show similar coupling rate as same as of the commercially available amidite reagent.

Using Klenow fragment (exo$^+$), incorporation of dYTP on dx2 in the template (refer to example 10).

Following base sequences were used as template and primer.

Primer (SEQ ID NO: 12)
5'-$^{32}$pACTCACTATAGGGAGGAAGA

Template (SEQ ID NO: 1, 7 or 8)
3'-TATTATGCTGAGTGATATCCCTCCTTCT-N-TCTCGT

Figure 12:
FIG. 12: Incorporation of various base against X2 of the present invention. Drawing is replaced by photograph.

In the template, a position indicated by N was bound with base X or base X2 (for experimental) or base A (for control), and incorporation experiments of various bases were conducted. Results are shown in FIG. 12, in which lanes 1 and 2 indicate control experiments for incorporation of cytosine (C) and thymine (T) on adenine (A).

Results indicate that rate of incorporation of dYTP on dx is 21% (lane 3), and that on dx2 is increased up to 40% (lane 8). As compared with the incorporation rate of 57% in the case of dTTP on natural type dA under the same condition, some improvement of incorporation was observed by using dx2. Although comparing with the case of dx, incorporation of dCTP is increased by using dx2 (22%) (lane 11), it is not so improved value as compared with the incorporation of dYTP (40%).

As a result of experiment using Klenow fragment (exo$^+$), incorporation rate of dCTP on dx2 was increased by using dx2 in place of dx. This might be due to interaction of 4-amino group of cytosine and sulfur atom in thiophene in dx2 (refer to FIG. 2f). As is the case that sulfur atom in thiophene of dx2 is directed to a plane of base pair, electrostatic repulsion against 4-keto group of thymine (T) will be expected. This indicates that electrostatic repulsive force (refer to FIG. 2e) can be used in addition to steric hindrance as a factor for hinder formation of base pairing. Accordingly, in thiophene in dx2, sulfur atom side might be directed to the plane of base pair.

Incorporation of rYTP into RNA on dx2 in the template by T7 RNA polymerase was examined according to the reaction (example 11):

13

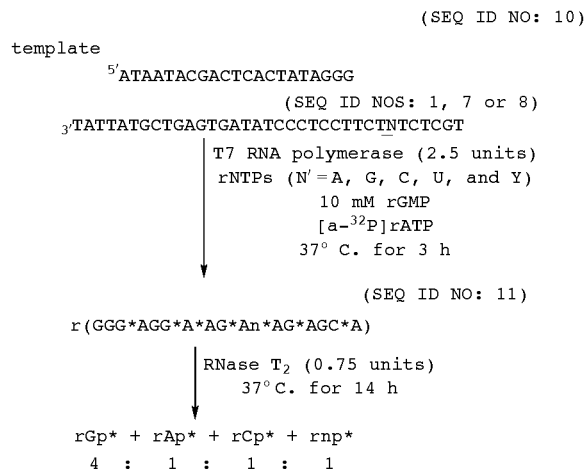

RNA having a sequence of the formula: (SEQ ID NO: 11)

GGG*AGG*A*AGAn*AG*AGC*A wherein n is a base corresponding to a base N, asterisk of the right shoulder means labeling, is digested by RNase T2, then ratio of each nucleotide was calculated by 2-diemntion TLC (cellulose resin).

Figure 13:
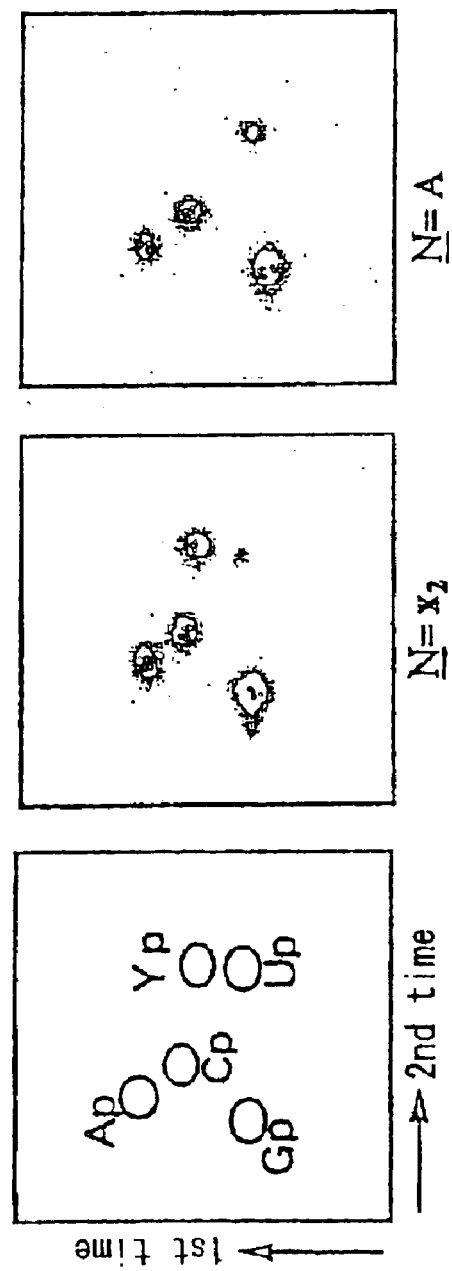
FIG. 13: Template containing X2 and rNTP were used. Generated RNA was purified by electrophoresis, then digestd with RNase T2 and analyzed by 2-dimention TLC.

In FIG. 13, development of TLC is shown. Ratio of composition of each nucleotide is shown in Table 2 hereinbelow.

TABLE 2

| Template | rGp* | rAp* | rCp* | rUp* | rYp* |
|---|---|---|---|---|---|
| N = x$_2$ | 3.982(4) | 1.052(1) | 0.950(1) | 0.047(0) | 0.969(1) |
| N = A | 3.939(4) | 1.035(1) | 0.995(1) | 1.032(1) | not detected(0) |

A parenthesis in the table indicates theoretical value.

Result indicates that using dx2, rYTP can be incorporated against dx2 with high selectivity. Good result has been obtained in case of using dx as a template in the previous experiment, and in case of using dx2 as a template to perform transcription in the similar condition, result of analysis on nucleotide incorporated in RNA on dx2 indicated that the similar high selectivity of incorporation of rYTP on dx2 was obtained.

As explained hereinabove, the present invention provides selective formation of base pair which has never achieved in the heretofore reported artificial base pair. Further, the present invention demonstrates that such the selective formation of base pair can be achieved by steric hindrance of base pair, preferably by applying steric hindrance and electrostatic repulsion as well as stacking action. Bases used in the above experiments are shown as illustration only of the present invention. This fact proves correctness of the idea of the present invention for achieving selective formation of artificial nucleic acid base pair. Consequently, the present invention is never limited within the bases concrete illustrated hereinbefore, and all base pairs generated according to the idea of the present invention are within the scope of the present invention.

Further, the fact that base pairs of the present invention could be recognized by natural synthetases has actually proved, and the base pairs of the present invention could also be used in synthetic and transcriptional systems of natural DNA and RNA as similar to the natural base pairs. Consequently, the present invention provides concept for formation of novel artificial base pair which can be applied and achieved in the systems on functional expression of natural gene. Such the artificial nucleic acid base pair of the present invention can be applied not only on the protein synthesis system or functional nucleic acid but also on the solution of functions and elucidation of natural gene systems.

EXAMPLES

Following examples illustrate the present invention but are not construed as limiting the present invention.

Example 1

Figure 3:
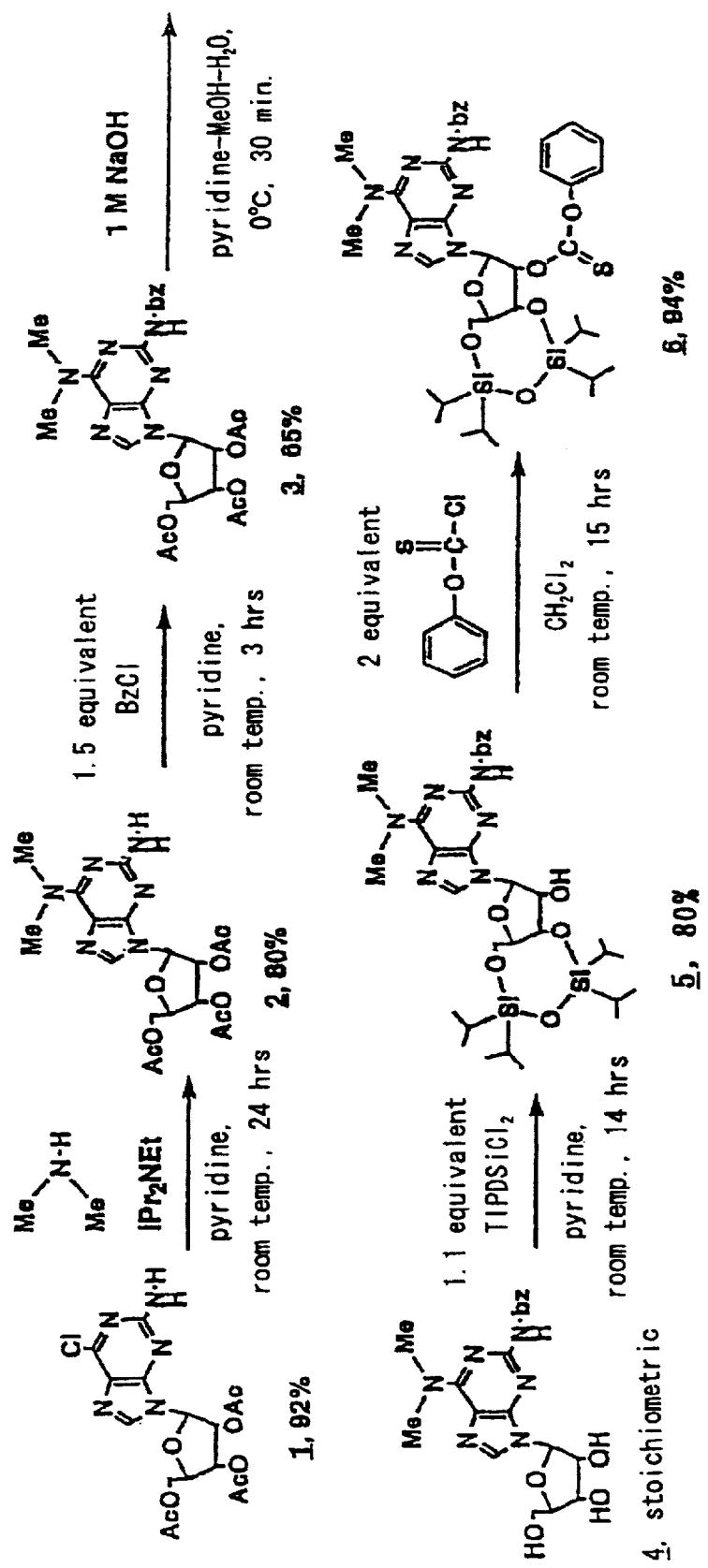
FIG. 3 shows synthetic scheme for amidite reagent for dX of nucleic acid having base X of the present invention.
Figure 3:
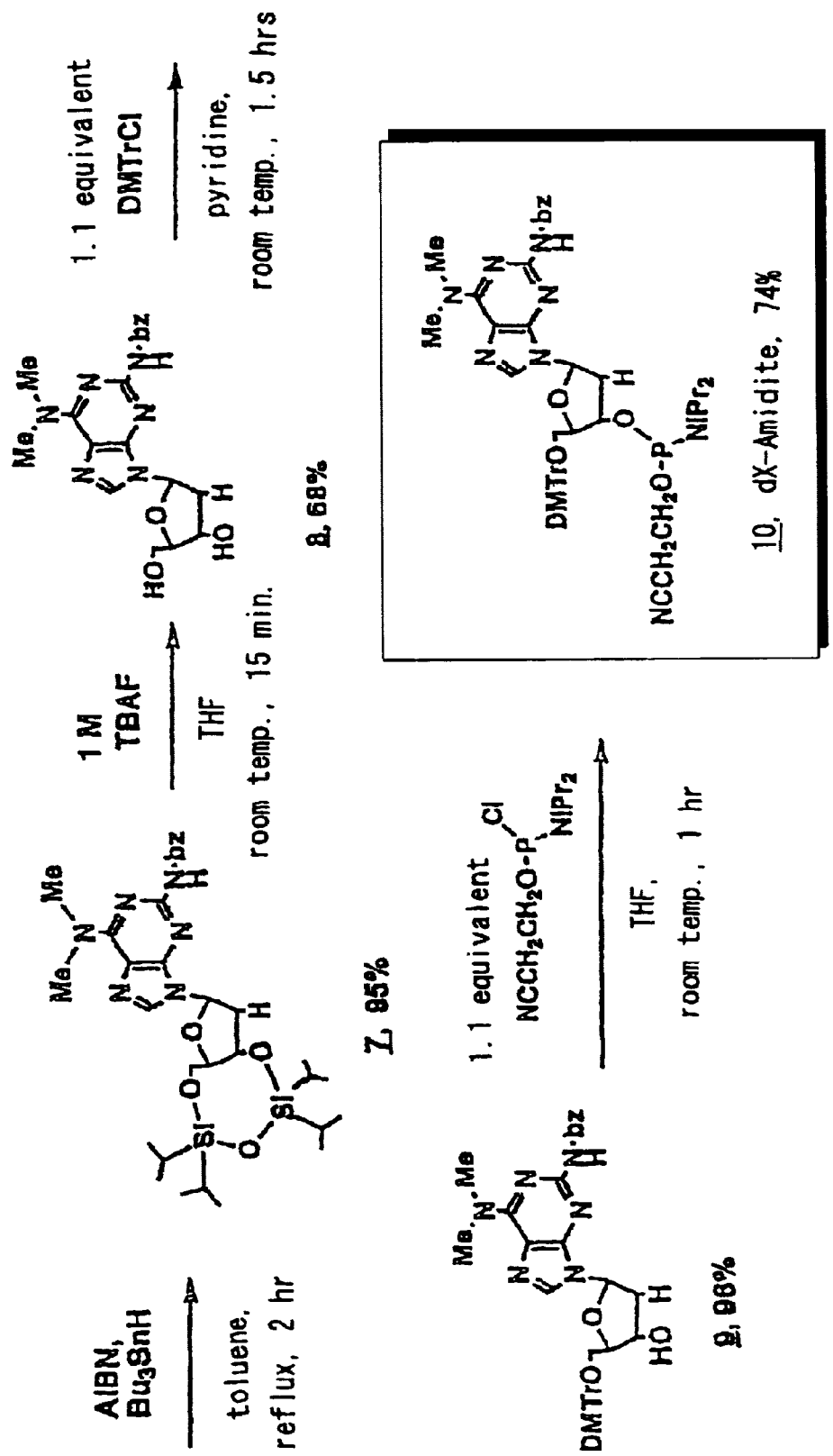

Synthesis of 2-benzamino-6-(N,N-dimethylamino)-9-[5'-O-dimethoxytrityl-3'-O-[[(diisopropylamino)-2-cyanoethoxy]phosphino]-2'-deoxy-β-D-ribofuranosyl] purine (10) (refer to FIG. 3)

(A) Synthesis of 2-amino-6-(N,N-dimethylamino)-9-(2',3,5'-tri-O-acetyl-β-D-ribofuranosyl]purine (2):

2-amino-chloro-9-(2',3',5'-tri-O-acetyl-β-D-ribofuranosyl)purine (1) [M. J. Robins and B. Uznanski, Can. J. Chem., 59, 2601–2607 (1981)1(18.6 mmol, 7.96 g) was dehydrated three times azeotropically with anhydrous pyridine, and dissolved in anhydrous pyridine (180 ml), then dimethylamine hydrochloride (55.8 mmol, 4.55 g) and diisopropylethylamine (74.4 mmol, 12.9 ml) were added thereto with stirring at room temperature. The mixture was stirred at room temperature for 15 hours. After confirming completion of the reaction by TLC, water was added to the reaction mixture and concentrated in vacuo. Chloroform was added to the residue, and the organic layer was washed 3 times with water, 2 times with 5% aqueous sodium hydrogen carbonate, once with water and 2 times with 10% aqueous citrate solution, then the organic layer was dried with magnesium sulfate, and dried in vacuo after filtration. The residue was treated with azeotropic distillation with toluene until no odor of pyridine was noted, the product was purified by silica-gel chromatography (dichloromethane-ethanol) to obtain the product (2) 5.42 g (12.4 mmol) (67%).

$^1$H-NMR (500.13 MHz, CDCl$_3$) δ: 7.56 (s, 1H, H8), 6.02 (d, 1H, H1', J=5.0 Hz), 5.95 (dd, 1H, H2', J=5.0 Hz), 5.79 (t, 1H, H3', J=5.0 Hz), 4.69 (s, 2H, 2-NH$_2$), 4.42–4.45 (m, 1H, H4'), 4.34–4.40 (m, 2H, H5', H5"), 3.43 (br, 6H, N—CH$_3$), 2.13, 2.10, 2.08 (s, 3H, Ac).

(B) Synthesis of 2-benzamino-6-(N,N-dimethylamino)-9-[2', 3', 5'-tri-O-acetyl-β-D-ribofuranosyl]purine (3)

A compound (2) obtained in the above (A) (10 mmol, 4.36 g) was azeotropically dehydrated three times and dissolved in anhydrous pyridine (180 ml). Under stirring at room temperature, benzoyl chloride (15 mmol, 1.74 ml) was added and the mixture was stirred at room temperature for 14 hours. After confirming completion of the reaction by TLC, water was added to the reaction mixture and concentrated in vacuo. Chloroform was added to the residue, and the organic layer was washed 2 times with 5% aqueous sodium hydrogen carbonate and once with water. The organic layer was dried with magnesium sulfate and filtered, then concentrated in vacuo. The residue was treated by azeotropic distillation until the residue showed no odor of pyridine. The residue was purified by silica-gel column chromatography (hexane-dichloroethane) to obtain the product (3) 3.53 g (6.53 mmol) (65%).

$^1$H-NMR (500.13 MHz, CDCl$_3$) δ: 8.46 (s, 1H, H8), 7.96 (d, 2H, Bz-m, J=10.0 Hz), 7.75 (s, 1H, NHBz), 7.55 (dd, 1H,

Bz-p, J=7.5 Hz), 7.48 (t, 2H, H Bz-o, J=7.5), 6.08 (d, 1H, H1', J=3.0 Hz), 5.96–6.01 (m, 2H, H2', H3'), 4.39–4.50 (m, 3H, H4', H5', H5"), 3.48 (br, GH, N—CH$_3$), 2.15 (s, 3H, Ac), 2.10 (s, 3H, Ac), 2.08 (s, 3H, Ac).

(C) Synthesis of 2-benzamino-6-(N,N-dimethylamino)-9-(β-D-ribofuranosyl)purine (4)

To a compound (3) obtained hereinabove (6.53 mmol, 3.53 g) pyridine-methanol-water (65:30:5) 50 ml was added and stirred in the ice-water bath. 2M sodium hydroxide-pyridine-methanol-water (65:30:5) 50 ml was added and stirred for 15 minutes in the ice-water bath. After confirming completion of the reaction, ammonium chloride (5.21 g) was added to the reaction mixture and concentrated in vacuo until volume reached up to 40 ml. Chloroform was added to the solution, and the organic layer was extracted. Then the aqueous layer was extracted twice with chloroform-pyridine. The organic layer was collected and dried with magnesium sulfate. The filtrate was concentrated up to volume of 10 ml in vacuo. Toluene was added thereto and concentrated in vacuo to precipitate crystals. Crystals were collected by filtration and dried in vacuo at 90° C. to obtain the product (4) 2.87 g.

$^1$H-NMR (500.13 MHz, DMSO-d$_6$) δ: 8.28 (s, 1H, H8), 7.92 (dd, 2H, Bz-m, J=7.0 Hz), 7.57 (dd, 1H, Bz-p, J=7.3 Hz), 7.49 (t, 2H, H Bz-o, J=7.5), 5.91 (d, 1H, H1', J=4.0 Hz), 5.48 (d, 1H, OH, J=5.5 Hz), 5.15 (d, 1H, OH, J=4.0 Hz), 5.04 (t, 1H, OH, J=1.0 Hz), 4.56 (t, 1H, H2', J=10.0 Hz), 4.17 (d, 1H, H3', J=3.0 Hz), 3.93 (d, 3H, H4', J=3.5 Hz), 3.63–3.65 (m, 1H, H5'), 3.52–3.56 (m, 1H, H5"), 3.48 (br, 6H, N—CH$_3$).

(D) Synthesis of 2-benzamino-6-(N,N-dimethylamino)-9-(3',5'-O-tetraisopropyldisiloxanyl-β-D-ribofuranosyl)purine (5)

A compound (4) obtained in the above (4) (5.0 mmol, 2.07 g) was dehydrated three times azeotropically with anhydrous pyridine and dissolved in anhydrous pyridine (50 ml), then 1,3-dichloro-1,1,3,3-tetraisopropyldisiloxane (5.5 mmol, 1.76 ml) was added and stirred at room temperature for 14 hours. After confirming completion of the reaction by TLC, water was added to the reaction mixture and concentrated in vacuo. Chloroform was added to the residue. The organic layer was washed twice with 5% aqueous sodium hydrogen carbonate and once with saturated sodium chloride solution. The organic layer was dried with magnesium sulfate, filtered and dried in vacuo. Azeotropic treatment was repeated until no odor of pyridine in the residue was noted. Then the residue was purified by silica-gel chromatography (dichloromethane-methanol) to obtain the product (5) 2.63 g (4.0 mmol) (80%).

$^1$H-NMR (500.13 MHz, CDCl$_3$) δ: 8.22 (s, 1H, H8), 7.89 (d, 2H, Bz-m, J=5.0 Hz), 7.80 (s, 1H, NHBz), 7.55 (dd, 1H, Bz-p, J=7.5 Hz), 7.48 (t, 2H, Bz-o, J=7.5 Hz), 5.91 (s, 1H, H1'), 4.84 (dd, 1H, H3', J=5.5 Hz), 4.50 (d, 1H, H2', J=5.5 Hz), 4.07–4.20 (m, 2H, H4', H5'), 4.06 (d, 1H, H5", J=13.0 Hz), 3.48 (br, 6H, N—CH3), 0.95–1.08 (m, 28H, iPr).

(E) Synthesis of 2-benzamino-6-(N,N-dimethylamino)-9-(2'-O-phenoxythiocarbonyl-3',5'-O-tetraisopropyldisiloxanyl-β-D-ribofuranosyl)purine (6)

The compound (5) obtained in the above (D) (3.98 mmol, 2.61 g) was dehydrated azeotropically three times with anhydrous toluene and dissolved in anhydrous dichloromethane (40 ml). 1-methylimidazole (7.96 mmol, 0.64 ml) and chlorothio carbonate phenyl (5.57 mmol, 0.77 ml) were added with stirring at room temperature, then stirred at room temperature for 16 hours. After confirming completion of the reaction by TLC, 5% aqueous sodium hydrogen carbonate was added to the reaction mixture. After extracted the organic layer, the organic layer was washed one with aqueous 5% sodium hydrogen carbonate, once with water, twice with aqueous 10% citrate solution and once with water, in this order, the organic layer was dried with magnesium sulfate, filtered and dried in vacuo. The residue was purified by silica-gel column chromatography (dichloromethane-methanol) to obtain the product (6) 2.96 g (3.73 mmol) (94%).

$^1$H-NMR (500.13 MHz, DMSO-d$_6$) δ: 8.17 (s,1H, H8), 7.87 (d, 2H, Bz-m, J=3.0 Hz), 7.79 (s, 1H, NHBz), 7.55 (t, 1H, Bz-p, J=7.5 Hz), 7.47 (t, 2H, H Bz-o, J=7.5 Hz), 7.41 (d, 2H, PhO-o, J=7.5 Hz), 7.29 (t, 2H, PhO-m, J=7.5 Hz), 7.13 (d, 1H, PhO-p, J=10.0 Hz), 6.39 (d, 1H, H2', J=5.0 Hz), 6.11 (s, 1H, HI'), 5.14–5.17 (m, 1H, H3'), 4.23–4.26 (m, 1H, H5'), 4.07–4.12 (m, 1H, H4', H5"), 3.48 (br, 6H, N—CH$_3$), 0.99–1.15 (m, 28H, iPr).

(F) Synthesis of 2-benzamino-6-(N,N-dimethylamino)-9-(2'-deoxy-3',5'-O-tetraisopropyldisiloxanyl-β-D-ribofuranosyl)purine (7)

The compound (6) obtained in the above (E) (3.73 mmol, 2.96 g) was dehydrated azeotropically three times with anhydrous toluene, and dissolved in anhydrous toluene (88 ml). 2,2'-azo-bis-isobutyronitrile (0.746 mmol, 122 mg) was added thereto with stirring at room temperature and added argon gas with bubbling for 1 hours at room temperature. Thereto was added tributyltin hydride (5.60 mmol, 1.51 ml) and stirred at 75° C. for 3.5 hours. After confirming completion of the reaction by TLC, the reaction mixture was concentrated in vacuo. The residue was purified by silica-gel column chromatography (diehloromethane-methanol) to obtain the product (7) 2.27 g (3.55 mmol) (95%).

$^1$H-NMR (500.13 MHz, CDCl$_3$) δ: 8.24 (s, 1H, H8), 7.90 (d, 2H, Bz-m, J:=5.0 Hz), 7.83 (s, 1H, NHBz), 7.54 (t, 1H, Bz-p, J=7.5 Hz), 7.48 (t, 2H, H Bz-o, J=7.5 Hz), 6.29 (dd, 1H, HI', J=7.5 Hz), 4.80–4.83 (m, 1H, H3'), 3.97–4.07 (m, 2H, H5', H5"), 3.86–3.88 (m, 1H, H4'), 3.50 (br, 6H, N—CH$_3$), 2.68–2.71 (m, 1H, H2'), 2.59–2.63 (m, 1H, H2"), 1.03–1.09 (m, 28H, iPr).

(G) Synthesis of 2-benzamino-6-(N,N-dimethylamino)-9-(2'-deoxy-βD-ribofuranosyl)purine (8)

The compound (7) obtained in the above (F) (3.55 mmol, 2.27 g) was added to 1M solution of tetrabutylammonium fluoride—tetrahydrofuran (14 ml) and stirred at room temperature for 15 minutes. After confirming completion of the reaction by TLC, the reaction mixture was concentrated in vacuo. The residue was dissolved in chloroform, washed with small amount of water, and the aqueous layer was extracted 4 times with chloroform. The organic layer was dried with magnesium sulfate. The filtrate was concentrated in vacuo and the residue was treated azeotropically with toluene until no odor of pyridine was noted. The residue was dissolved in methanol. Dichloromethane was added dropwise as little as possible to crystallize the product. The crystals were collected by filtration and dried in vacuo to obtain the product (8) 0.964 g (2.42 mmol) (68%).

$^1$H-NMR (500.13 MHz, DMSO-d$_8$) δ: 8.23 (s, 1H, H8), 7.84 (d, 2H, Bz-m, J=7.5 Hz), 7.50 (t, 1H, Bz-p, J=7.3 Hz), 7.42 (t, 2H, H Bz-o, J=7.5 Hz), 6.25 (t, 1H, H1', J=7.0 Hz), 5.21 (s,1H, OH), 4.89 (s, 1H, OH), 4.33 (s, 1H, H3'), 3.77 (s, 1H, H4'), 3.50–3.53 (m, 1H, H5'), 3.43–3.46 (m, 1H, H5"), 3.48 (br, 6H, N—CH$_3$), 2.56–2.61 (m, 1H, H2'), 2.16–2.18 (m, 1H, H2").

(H) Synthesis of 2-benzamino-6-(N,N-dimethylamino)-9-(5'-O-dimethoxytrityl-2'-deoxy-β-D-ribofuranosyl)purine (9)

The compound (8) (1.47 mmol, 0.585 g) was azeotropically dehydrated three times with anhydrous pyridine and dissolved in anhyride pyridine (10 ml). 4,4'-dimethoxy tritylchloride (1.61 mmol, 547 mg) was added with stirring at room temperature, then stirred at room temperature for 1.5 hours. After confirming completion of the reaction by TLC, water was added to the reaction mixture and concentrated in vacuo. Chloroform was added to the residue and the organic layer was washed twice with aqueous 5% sodium hydrogen carbonate and once with water, then the organic layer was dried with magnesium sulfate, filtered and concentrated in vacuo. The residue was azeotropically distilled with toluene until no odor of pyridine was noted, and was purified by silica-gel column chromatography (dichloromethane-methanol-0.5% triethylamine) to obtain the product (9) 0.99 g (1.41 mmol) (96%).

$^1$H-NMR (270.16 MHz, CDCl$_3$) δ: 8.20 (s,1H, H8), 7.79 (s, 1H, NHBz), 7.77 (d, 2H, Bz-m, J=1.4 Hz), 7.76 (d, 1H, Bz-p, J=3.5 Hz), 7.14–7.51 (m, 11H, H Bz-o, DMTrI, 6.72 (dd, 4H, DMTr), 6.45 (t, 1H, HI', J=6.5 Hz), 4.78 (m, 1H, H3'), 4.14 (m, 1H, 114'), 3.74 (s, 6H, OCH$_3$), 3.50 (br, 6H, N—CH$_3$), 3.39–3.47 (m, 1H, H5'), 3.30–3.33 (m, 1H, H5"), 2.80–2.85 (m, 2H, H2', H2").

(I) Synthesis of 2-benzamino-6-(N,N-dimethylamino)-9-[5'-O-dimethoxytrityl-3'-O-[[((diisopropylamino)-2-cyanoethoxy]phosphino]-2'-deoxy-β-D-ribofuranosyl]purine (10)

The compound (9) (0.864 mmol, 0.605 g) was azeotropically distilled three times with anhydrous pyridine and twice with anhydrous tetrahydrofuran and dissolved in anhydrous tetrahydrofuran (6 ml). N,N-diisopropylethylamine (2.59 mmol, 0.452 ml) and chloro-2-cyanoethoxy-N,N-diisopropyl-aminophosphine (1.73 mmol, 0.385 ml) were added with stirring at room temperature and further stirred at room temperature for 2 hours. After confirming completion of the reaction by TLC, anhydrous methanol was added to the reaction mixture to terminate the reaction. Ethyl acetate was added to the reaction mixture, and the organic layer was washed once with 5% aqueous sodium hydrogen carbonate and three times with saturated aqueous sodium chloride solution. The organic layer was dried with anhydrous sodium sulfate and concentrated in vacuo after filtration. The residue was purified by silica-gel column chromatography (dichloromethane-methanol-2% triethylamine), and dissolved in small volume of chloroform, and reprecipitated by adding hexane to obtain the product (10) 0.574 g (0.638 mmol) (74%).

$^1$H-NMR (270.16 MHz, CDCl$_3$) δ: 8.14 (s, 1H, H8), 8.13 (s, 1H, H8), 7.72 (s, 1H, NHBz), 7.65–7.70 (m, 2H, Bz-m), 7.16–7.47 (m, 12H, H Bz-p, o, DMTr), 6.70–6.75 (m, 4H, DMTr), 6.27–6.41 (m, 1H, H1'), 4.63–4.80 (m, 1H, H3'), 4.20–4.27 (m, 1H, H4'), 3.74 (s, 6H, OCH$_3$), 3.24–3.72 (m, 1OH, H5', H5", NCH(CH$_3$)$_2$, N—CH$_3$), 2.83–3.00 (m, 1H, H2'), 2.40–2.64 (m, 5H, H2", OCH$_2$CH$_2$CN), 1.06–1.19 (m, 12H, NCH(CH$_3$)$_2$).

31P-NMR (109.36 MHz, CDCl$_3$) δ: 149.25.

Example 2

Synthesis of 2-isobutyrylamino-6-(2-thienyl)-9-[2-deoxy-3-O-[diisopropylamino]-(2-cyanoethoxy)]phosphino-5-O-dimethoxytrityl-β-D-ribofuranosyl]purine (22) (Synthetic Route is Shown in FIG. 5)

(A) Synthesis of 2-isobutyrylamino-6-iodo-9-(2-deoxy-3,5-di-O-isobutyryl-β-D- ribofuranosyl]purine (18)

2-isobutyrylamino-6-amino-9-(2-deoxy-3,5-di-O-isobutyryl-β-D-ribofuranosyl)purine (17) [Babara L. Gaffney, Luis A. Marky and Roger A. Jones, Tetrahedron, 40, 3–13 (1984)] 2.38 g (5 mmol) was heated at 60° C. under argon atmosphere. n-pentylnitrite 13.5 ml (0.10 mol) and diiodomethane 25 ml (0.31 mol) were rapidly added and suspended. The mixture was irradiated by visible light using 200 W halogen tungsten lump at the distance from light source 2 cm for 3 hours under well stirring at 60° C. To the reaction mixture, saturated aqueous sodium sulfite 30 ml was added and stirred at room temperature for 3 hours. Thereafter, saturated aqueous sodium sulfite 120 ml and chloroform 150 ml were added to separate the layers. The aqueous layer was extracted twice with chloroform. The thus obtained organic layer was dried with anhydrous magnesium sulfate and concentrated. The residue was purified by short column (developer: ethyl acetate:dichloromethane=1:4) to obtain the product (18) 1.01 g (1.72 mmol) (34.4%).

$^1$H-NMR (270 MHz, CDCl$_8$) δ: 8.19 (s, 1H), 8.14 (bs, 1H), 6.42 (dd, J=7.4, 6.4 Hz, 1H), 5.44 (m, 1H), 4.41 (m, 2H), 4.34 (m, 1H), 3.00 (m, 1H), 2.80 (m, 1H), 2.58 (m, 3H), 1.17 (m, 18H).

(B) Synthesis of 2-isobutyrylamino-6-(2-thienyl)-9-(2-deoxy-3,5-di-O-isobutyryl-δ-D-ribofuranosyl)purine (19)

The compound (18) 294 mg (0.5 mmol) obtained in the above (A) was dissolved in thiophene 80 ml under argon atmosphere and the solution was transferred into the photochemical reaction vessel (Pyrex). Ultraviolet ray was irradiated using 400 W mercury lamp for 24 hours under argon atmosphere. The reaction mixture after irradiation was concentrated, and the residue was purified using short column (developer: isopropanol:dichloromethane=3:197) to obtain the product (19) 212 mg (0.39 mmol) (78.0%).

$^1$H-NMR (270 MHz, CDCl$_3$) δ: 8.63 (dd, J=3.8, 1.2Hz, 1H), 8.17 (s, 1H), 8.10 (bs, 1H), 7.64 (m, 1H), 7.25 (m, 1H), 6.47 (dd, J=7.9, 1.8 Hz, 1H), 5.44 (m, 1H), 4.43 (m, 2H), 4.37 (m, 1H), 3.18 (m, 1H), 3.00 (m, 1H), 2.61 (m, 3H), 1.24 (m, 18H).

(C) Synthesis of 2-isobutyrylamino-6-(2-thienyl)-9-(2-deoxy-β-D-ribofuranosyl)purine (20)

The compound (19) 212 mg (0.39 mmol) obtained by the above (B) was dissolved in 1 M sodium hydroxide solution (pyridine-methanol-water=13:6:1) 1.95 ml under ice-cooling and stirred for 15 minutes. The reaction mixture was neutralized by adding aqueous 5% ammonium chloride. Further added 1.2 g Celite to the mixture and the solvent was removed completely under reduced pressure. The residue was purified by short column (developer: 5-7% ethanol-dichloromethane) to obtain the product (20) 147 mg (0.37 mmol) (93.6%).

$^1$H-NMR (270 MHz, DMSO-d$_6$) δ: 10.45 (bs, 1H), 8.69 (s, 1H), 8.60 (d, J=3.5 Hz, 1H), 7.90 (d, J=4.6 Hz, 1H), 7.32 (dd, J=4.6, 3.5 Hz, 1H), 6.39 (t, J=6.6 Hz, 1H), 5.34 (d, J=3.8 Hz, 1H), 4.91 (t, J=5.3 Hz, 1H), 4.44 (m, 1H), 3.55 (m, 2H), 2.96 (m, 1H), 2.74 (m, 1H), 2.33 (m, 1H), 1.11 (m, 6H).

(D) Synthesis of 2-isobutyrylamino-6-(2-thienyl)-9-(2-deoxy-5-O-dimethoxytrityl-β-D-ribofuranosyl)purine (21)

The compound (20) 98 mg (0.24 mmol) obtained in the above (C) was azeotropically distilled three times with anhydrous pyridine (1 ml). The residue was dissolved in anhydrous pyridine 2 ml, added triethylamine 35 ml, dimethylaminopyridine 1.4 mg and dimethoxytrityl chloride 85 mg were added thereto and stirred at room temperature for overnight. Ethyl acetate 25 ml was added to the reaction mixture. The mixture was treated with water (25 ml) for three time for separation to obtain organic layer. Each aqueous layer was washed with ethyl acetate. The organic layer was collected, dried with anhydrous sodium sulfate and concentrated in vacuo. The residue was purified by using short column (developer: 25-50% ethyl acetate-dichloromethane) to obtain the product (21) 132 mg (0.19 mmol) (76.7%).

¹H-NMR (270 MHz, CDCl) δ: 8.64 (dd, J=3.6, 0.9 Hz, 1H), 8.14 (s, 1H), 7.92 (bs, 1H), 7.61 (dd, J=4.3, 0.9 Hz, 1H), 7.39 (m, 2H), 7.24 (m, 8H), 6.77 (m, 4H), 6.47 (t, J=6.2 Hz, 1H), 4.79 (m, 1H), 4.13 (m, 1H), 3.76 (s, 3H), 3.75 (s, 3H), 3.44 (dd, J=10.23, 5.8 Hz, 1H), 3.38 (dd, J=10.23, 4.4 Hz, 1H), 2.91 (m, 1H), 2.60 (m, 1H), 2.30 (m, 1H), 1.27 (m, 6H).

(E) Synthesis of 2-isobutyrylamino-6-(2-thienyl)-9-2-deoxy-3-O-[(diisopropylamino)-(2-cyanoethoxy)]phosphyno-5-O-dimethoxytrityl-β-D-ribofuranosyl)purine (22)

The compound (21) 125 mg (0.18 mmol) obtained in the above (D) was azeotropically distilled three times with anhydrous pyridine 0.5 ml and azeotropically distilled three times with anhydrous tetrahydrofuran 0.5 ml. The residue was dissolved in anhydrous tetrahydrofuran 1.2 ml under argon atmosphere, then added further diisopropylethylamine 46 ml and (2-cyanoethoxy)(N,N-diisopropylamino)phosphine chloride 59 ml and stirred at room temperature for 1 hour. Remained chloride was decomposed by adding methanol 50 ml. Ethyl acetate containing 3% triethylamine 25 ml was added to the reaction mixture, and water 25 ml was added for three times separation to obtain organic layer. Each aqueous layer was washed with 3% triethylamine containing ethyl acetate. The organic layer was collected, dried with anhydrous sodium sulfate and concentrated in vacuo. The residue was purified by using short column (developer: 3% triethylamine-32% ethyl acetate-65% hexane) to obtain the product (22) 139 mg (0.16 mmol) (92.2%).

¹H-NMR (270 MHz, CDCl₃) δ: 8.64 (m, 1H), 8.16 (m, 1H), 7.86 (m, 1H), 7.61 (m, 1H), 7.26 (m, 2H), 7.24 (m, 8H), 6.78 (m, 4H), 6.45 (m, 1H) 9, 4.75 (m, 1H), 4.23 (m, 1H), 3.75 (m, 6H), 3.70 (m, 4H), 3.36 (m, 2H), 2.75 (m, 2H), 2.62 (m, 1H), 2.48 (m, 1H), 1.95 (m, 1H), 1.18 (m, 18H).

³¹P-NMR (270 MHz, CDCl₃): 149.51, 148.43 ppm.

Example 3

Synthesis of 3-(2'-deoxy-5'-O-triphosphoryl-βD-ribofuranosyl)pyridine-2-one (dYTP) (23) (Refer to FIG. 4)
(A) Synthesis of 3-(3',5'-O-tetraisopropyldisiloxanyl-β-D-ribofuranosyl)pyridine-2-one (12)

3-(β-D-ribofuranosyl)pyridine-2-one (11) [J. Matulic-Adamic and L. Beigelman, Tetrahedron Lett., 38, 203–206 (1997)](2.29 mmol, 520 mg) was azeotropically dehydrated three times with anhydrous pyridine and was dissolved in anhydrous pyridine (23 ml). 1,3-dichloro-1,1,3,3-tetraisopropyldisiloxane (2.52 mmol, 0.81 ml) was added with stirring at room temperature and further stirred at room temperature for overnight. After confirming completion of the reaction by TLC, water was added to the reaction mixture to terminate the reaction and concentrated in vacuo. The residue was dissolved in chloroform. The organic layer was washed twice with aqueous 5% sodium hydrogen carbonate and once with aqueous saturated sodium chloride solution. The organic layer was dried with magnesium sulfate, and filtered. The filtrate was concentrated in vacuo. The residue was purified by using silica-gel chromatography (dichloromethane-methanol) to obtain the product (12) 442 mg (0.94 mmol) (41%).

¹H-NMR (270.06 MHz, CDC₃) δ: 13.07 (br, 1H, NH), 7.78 (d, 1H, H4, J=6.8 Hz), 7.37 (d, 1H, H6, J=4.6 Hz), 6.29 (t, 1H, H5, J=6.6 Hz), 5.07 (s, 1H, H1'), 4.01–4.30 (m, 5H, H2', H3', H4', H5', H5"), 0.83–1.10 (m, 28H, iPr).

(B) Synthesis of 3-(2'-O-imidazothiocarbonyl-3',5'-O-tetraisopropyldisiloxanyl-β-ribofuranosyl)pyridine-2-one (13)

The compound (12) (0.94 mmol, 442 mg) obtained in the above (A) was dehydrated azeotropically three times with anhydrous toluene, dissolved in anhydrous DMF (9 ml). Thiocarbonylimidazolide (2.24 mmol, 401 mg) was added under stirring at room temperature, then the reaction mixture was stirred at room temperature for 7 hours. After confirming completion of the reaction by TLC, ethyl acetate was added to the reaction mixture. The organic layer was washed twice with water, dried with magnesium sulfate, and the filtrate was concentrated in vacuo. The residue was purified by using silica-gel column chromatography (dichloromethane-methanol) to obtain the product (13) 434 mg (0.749 mmol) (80%).

¹H-NMR (270.06 MHz, CDCl₃) δ: 13.40 (br, 1H, NH), 8.44 (s, 1H, imidazolide), 7.84 (d, 1H, H4, J=6.8 Hz), 7.73 (s, 1H, imidazolide), 7.33 (d, 1H, H6, J=6.5 Hz), 7.07 (s, 1H, imidazolide), 6.34 (t, 1H, H5, J=6.8 Hz), 6.23 (d, 1H, H2', J=5.1 Hz), 5.25 (s, 1H, H1'), 4.46–4.52 (m, 1H, H3'), 4.25–4.29 (m, 1H, H5'), 4.03–4.09 (m, 2H, H4', H5"), 0.87–1.09 (m, 28H, iPr).

(C) Synthesis of 3-(2'-deoxy-3',5'-O-tetraisopropyldisiloxanyl-β-ribofuranosyl)pyridine-2-one (14)

The compound (13) (0.749 mmol, 434 mg) obtained in the above (B) was dehydrated azeotropically three times with anhydrous toluene, added ammonium sulfate (8.4 mg), dissolved in hexamethyldisilazane (12.6 ml) and refluxed for 1 hour. The reaction mixture was concentrated in vacuo, dehydrated azeotropically three times with anhydrous toluene, added azobisisobutyronitrile (83.5 mg) and dissolved in anhydrous toluene (16.8 ml). Tributyltin hydride (0.821 ml) was added to the reaction mixture and refluxed for 1 hour. After confirming completion of the reaction by TLC, the reaction mixture was concentrated in vacuo. The residue was purified by using silica-gel column chromatography (dichloromethane-methanol) to obtain the product (14) 0.268 g (0.591 mmol) (79%).

¹H-NMR (270.06 MHz, CDCl₃) δ: 13.07 (br, 1H, NH), 7.72 (d, 1H, H4, J=7.0 Hz), 7.31 (d, 1H, H6, J=6.5 Hz), 6.29 (t, 1H, H5, J=6.6 Hz), 5.20–5.25 (m, 1H, H1'), 4.37–4.40 (m, 1H, H3'), 3.97–4.12 (m, 2H, H5', H5"), 3.80–3.84 (m, 1H, H4'), 2.26–2.36 (m, 1H, H2'), 1.77–1.86 (m, 1H, H2"), 0.90–1.09 (m, 28H, iPr).

(D) Synthesis of 3-(2'-deoxy-β-D-ribofuranosyl)pyridine-2-one (15)

The compound (14) (0.089 mmol, 42 mg) obtained in the above (C) was dehydrated azeotropically three times with anhydrous toluene, added 1 M tetramethyl ammoniumfluoride/THF solution (0.5 ml) and stirred at room temperature for 2 hours. After confirming completion of the reaction by TLC, acetic acid (0.08 ml) was added thereto and concentrated in vacuo. The residue was dissolved in water, washed three times with ethyl acetate, and the aqueous layer was concentrated in vacuo. The residue was purified by using reverse phase silica-gel chromatography to obtain the product (15) 10.4 mg (0.047 mmol) (52%).

¹H-NMR (270.06 MHz, CDCl₃) δ: 7.77 (d, 1H, H4, J=3.8 Hz), 7.36 (d, 1H, H6, J=3.5 Hz), 6.41 (t, 1H, H5, J=3.6 Hz), 5.01–5.17 (m, 1H, H1'), 4.29–4.31 (m, 1H, H3'), 3.93–3.95 (m, 1H, H4'), 3.62–3.70 (m, 2H, H5', H5"), 2.31–2.35 (m, 1H, H2'), 1.89–1.95 (m, 1H, H2").

(E) Synthesis of 3-(2'-deoxy-5'-O-triphosphoryl-β-D-ribofuranosyl)pyridine-2-one (16)

The compound (15) (0.059 mmol, 13.4 mg) obtained in the above (D) was dehydrated azeotropically three times with anhydrous toluene, dissolved in trimethyl phosphate (0.2 ml), added phosphorus oxychloride (0.065 mmol, 7.1 μl) under ice-cooling and stirred for 7 hours under ice-cooling. After confirming completion of the reaction by TLC, well mixed solution of 0.5 M bistributylammonium pyrophosphate-DMF solution and tributylamine (70.2 µl) was immediately added and stirred well under ice-cooling for 30 minutes. 1 M triethylammonium bicarbonate (0.35 ml) was added to the reaction mixture to terminate the reaction and concentrated in vacuo. The residue was dissolved in water and charged on a column of DEAE-Sephadex chromatography (15×300 mm) and eluted by gradient elution with 50 mM–1 M triethylammonium bicarbonate. A fraction eluted at 0.53–0.59 M was collected and lyophilized. Structure was confirmed by MS (ESI-), $^1$H-NMR and $^3$P-NMR. Sodium salt was prepared by treating with Dowex 50W×8 column chromatography. MS (ESI-): (M-H$^+$) 449.9.

$^1$H-NMR (270.06 MHz, CDCl$_3$) δ: 7.83 (d, 1H, H4, J=4.9 Hz), 7.35 (d, 1H, H6, J=4.9 Hz), 6.51 (t, 1H, H5, J=4.9 Hz), 5.17 (t, 1H, H1', J=5.0 Hz), 4.56 (br, 1H, H3'), 4.06 (br, 1H, H4'), 3.99 (br, 2H, H5', H5"), 2.19–2.33 (m, 1H, H2'), 1.81–1.98 (m, 1H, H2").

$^{31}$P-NMR (109.36 MHz, D$_2$O) δ: –10.3 (m, 2P, P$^1$, P$^3$), –22.7 (m, 1P, P$^2$), UV (10 mM phosphate buffer pH 7.0): λmax=298 nm (ϵ=7.6×10$^3$), 226 nm (ϵ=7.0×10$^3$), λmin=247 nm, 211 nm.

Example 4

Synthesis of Primer and Template

Following primer and template were synthesized conventionally by using DNA/RNA synthesizer Type 392, The Perkin-Elmer, Applied Biosystems Div., and cyanoethylamidide reagents of dA, dC, dG and dT, which were available from The Perkin-Elmer, and dX of cyanoethylamidide reagent hereinbefore.

Proviso that in a synthesis of oligomer containing dX, removal of protective group for amino group of dX, i.e. benzoyl group, could not completely be performed by conventional condition using conc. ammonia at 55° C. for overnight, consequently, treatment for removal of the protective group was performed under the condition at 80° C. with conc. ammonia for 10 hours.

Primer 1: (SEQ ID NO: 13) dcgactcactataggg
Primer 2: (SEQ ID NO: 14) dctatagggaggaga
Primer 3: (SEQ ID NO: 15) dgcctagttgtaccg
Template 1: (SEQ ID NO: 7) dtgctctatcttcctccctatagt-gagtcgtattat
Template 2: (SEQ ID NO: 8) dtgctctgtcttcctccctatagt-gagtcgtattat
Template 3: (SEQ ID NO: 1) dtgctctxtcttcctccctatagt-gagtcgtattat
Template 4: (SEQ ID NO: 9) dagctgtgtgtgtctccggtacaac-taggc
Template 5: (SEQ ID NO: 2) dagctxtgtgtgtctccggtacaac-taggc
Template 6: (SEQ ID NO: 3) dagctxxgtgtgtctccggtacaac-taggc
Template 7: (SEQ ID NO: 4) dagctxtxtgtgtctccggtacaac-taggc
Template 8: (SEQ ID NO: 5) dagctxtgxgtgtctccggtacaac-taggc
Template 9: (SEQ ID NO: 6) dagctxtgtxtgtctccggtacaac-taggc Example 5

5'-$^{32}$P Labeling of Primer

Primer 1–4 (ca. 1 nmol), 10×polynucleotide kinase buffer (TAKARA) 2 µl, [γ-$^{32}$ P]-dATP (ca. 1.1 TBq/mmol) 2 µl, and polynucleotide kinase (10 unit/µl, TAKARA) 2 µl were added into a tube 0.5 ml. The mixture, total 20 µl, was incubated at 37° C. for 40 minutes. The reaction was terminated by adding 10 M urea BPB dye 10 µl, treated at 75° C. for 5 minutes, then electrophoresed using 20% polyacrylamide 7M urea gel electrophoresis (10 cm×10cm). Main band detected by UV (254 nm) was cut out, transferred to 1.5 ml tube, adding 450 µl of sterilized water ant stirred at 37° C. for 12 hours. Supernatant obtained by light centrifugation was transferred to the different tube, added glycogen 1 µl, 3M sodium acetate 40 µl and ethanol 1 ml were added. The mixture was shaken well, thereafter allowed to stand at –30° C. for 1 hour. Then it was centrifuged at –5° C., under 13,000 rpm for 1 hours. The thus obtained precipitate was rinsed with 70% ethanol and dried by using centrifugal evaporator for 30 minutes. Sterilized water 40 µl was added and kept at 75° C. for 5 minutes, thereafter quantitated at UV 260 nm.

Example 6

Figure 9:
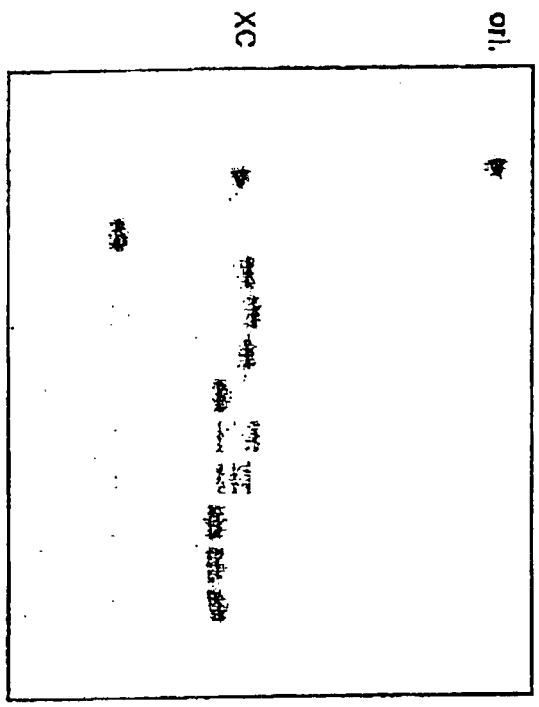
FIG. 9 shows primer extension reaction by Klenow fragment using 5'-terminal $^{32}$P labeled primer 3 (0.33 μμM) and template 4, 5, 6, 7, 8, and 9 (1 μM) and various dNTP (150 μM). Reaction was performed at 17° C. for 60 minutes.
Figure 9:
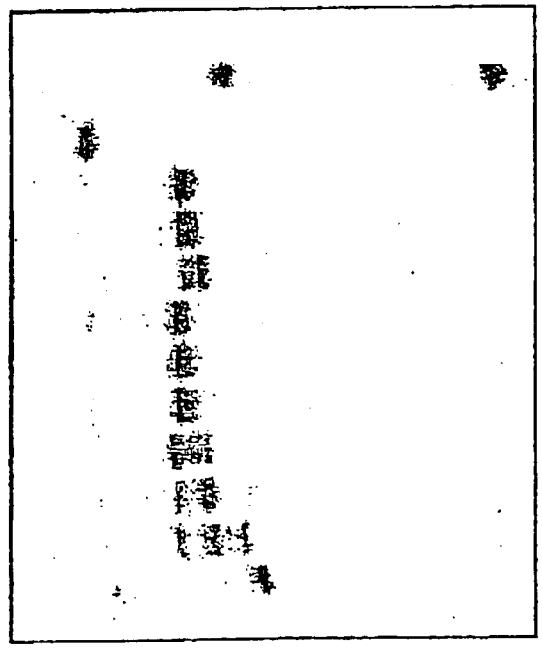

Single Nucleotide Insertion Reaction and Primer Extension Reaction Using Klenow Fragment 5'-$^{32}$P labeled primer, template and 10×Klenow fragment buffer (TAKARA) 1 µl were added to the 0.5 ml tube, adjusted total volume to 7 µl, and annealed at 95° C. for 3 minutes, at 40° C. for 3 minutes and at 4° C. for 7 minutes. dNTP 1 µl, Klenow fragment (1 unit/ml, For Sequencing, TAKARA) 2 µl were added, adjusted to total volume to 10 µl and incubated for the fixed time at 17° C. The reaction was terminated by adding 10M urea BPB dye 5 µl, heated at 75° C. for 5 minutes, and electrophoresed with 20% polyacrylamide gel with 7M urea gel electrophoresis. The result was analyzed using imaging plates (Phosphoroimager analysis). Results are shown in FIG. 6, FIG. 7 and FIG. 9. Single nucleotide insertion reaction is shown in FIG. 7 and primer extension reaction is shown in FIG. 6 and FIG. 9, respectively.

Example 7

Inhibition Experiment For Primer Extension Reaction Using Klenow Fragment

Figure 8:
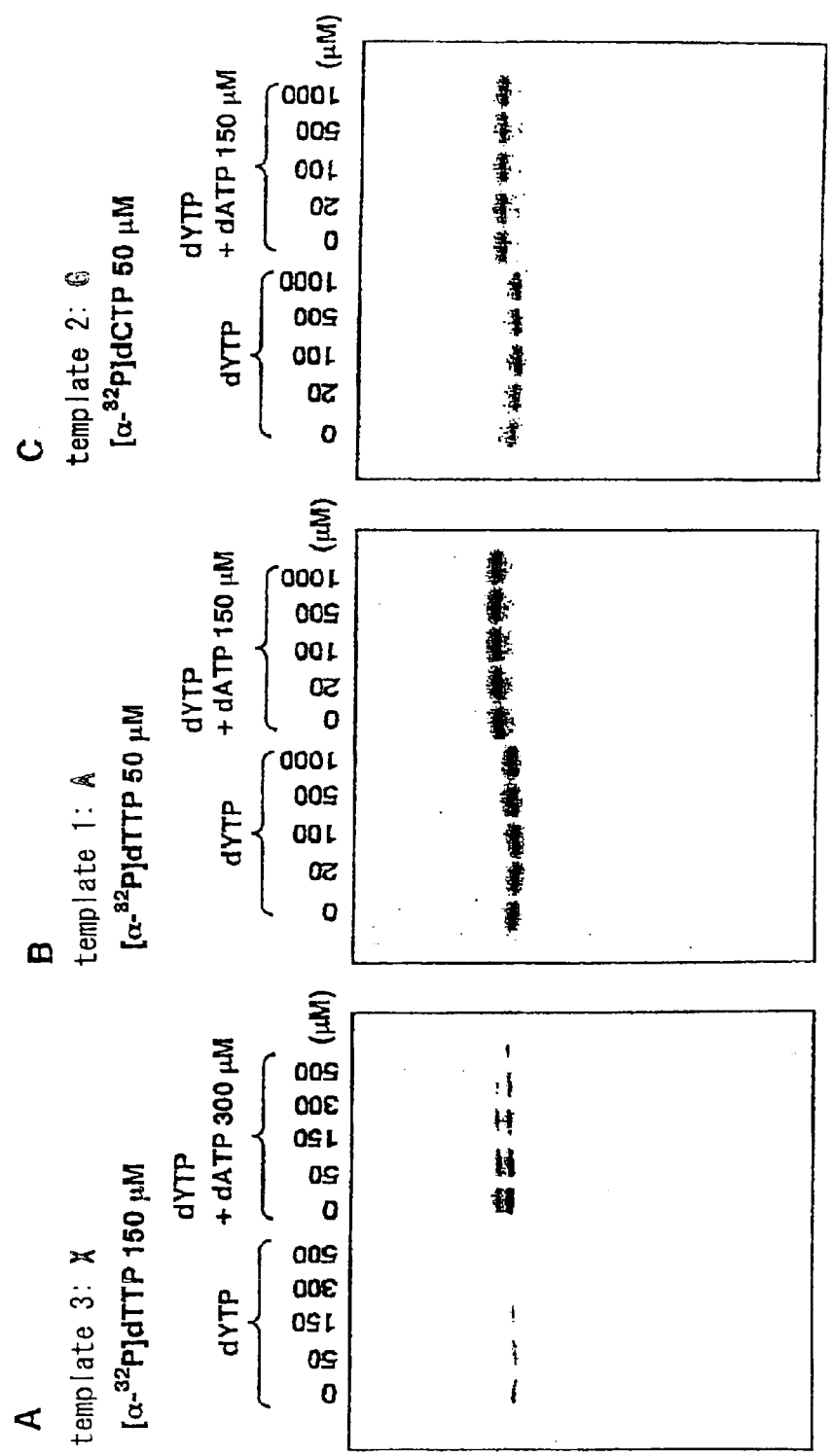
FIG. 8 shows inhibitory experiment by dYTP on primer extension reaction by Klenow fragment using primer 2, template 1, 2, 3 and [α-$^3$P]TTP or [a-$^{32}$P]dCTP.
A: Primer extension reaction by Klenow fragment was performed at 17° C. for 30 minutes. Primer 2 (1 μM), template 3 (2 μM) and [α-$^{32}$P]TTP (150 μM) are used. dYTP, 0, 50, 150, 300 and 500 μM are added.
Right lane 5: same experiment was performed by adding dATP (300 μM)
B: Primer extension reaction by Klenow fragment was performed at 17° C. for 10 minutes. Primer 2 (1 μM), template 1 (2 μM) and [α-$^{32}$P]TTP (50 μM) are used. dYTP, 0, 20, 100, 500 and 1000 μM are added.
Right lane 5: same experiment was performed by adding dATP (300 μM)
C: Primer extension reaction by Klenow fragment was performed at 17° C. for 30 minutes. Primer 2 (1 μM), template 2 (2 μM) and [α-$^{32}$P]TTP (50 μM) are used. dYTP, 0, 20, 100, 500 and 1000 μM are added.
Right lane 5: same experiment was performed by adding dATP (300 μM)

Primer, template and 10×Klenow fragment buffer (TAKARA) 1 µl were added to 0.5 ml tube, and total volume was adjusted to 7 µl, and annealed at 95° C. for 3 minutes, at 40° C. for 3 minutes and at 4° C. for 7 minutes. [α-$^{32}$P]TTP or [α-$^{32}$P]dCTP and dYTP were added to final concentration for each level, and Klenow fragment (1 unit/ml, For Sequencing, TAKARA) 2 µl was added, adjusted to total volume to 10 µl and incubated for the fixed time at 17° C. The reaction was terminated by adding 10 M urea BPB dye 5 µl, kept at 75° C. for 5 minutes, and electrophoresed with 20% polyacrylamide gel with 7M urea gel electrophoresis. The result was analyzed using imaging plates (Phosphoroimager analysis). Result is shown in FIG. 8.

Example 8

Transcription by T7 RNA Polymerase

Template DNA 1 µM, in which promoter region has duplicated strands, and T7 RNA polymerase 2.5 units were added to a solution containing 2 mM rNTP, [α-$^{32}$P]ATP 0.1 αCi/µl [40 mM Tris-HCl (pH 8.0), 8 mM MgCl$_2$, 2 mM spermidine, 5 mM DTT, 0.01% Triton X-100, 10 mM rGMP], and incubated for 3 hours. After the reaction, 10 M urea dye was added and kept at 75° C. for 3 minutes, then electrophoresed with 20% polyacrylamide gel. The product was analyzed. Result is shown in FIG. 10.

Example 9

Transcription Using T7 RNA Polymerase

Reaction was performed as same as in example 8. The generated RNA was isolated by gel electrophoresis. RNA was digested by 0.75 units RNase T2. Each nucleotide was separated using 2-dimension TLC and each ratio was calculated.

Result is shown in FIG. 11. Ratio of composition of each nucleotide is shown in Table 1 hereinbefore.

Example 10

Single Nucleotide Insertion Reaction Using Klenow Fragment (exo+)

A solution containing [5'-$^{32}$P] labeled primer DNA (20-mer, 4 mM), template DNA (35-mer, 4 mM) and 2×Klenow fragment buffer (TAKARA) were annealed at 95° C. for 3 minutes, 40° C. for 3 minutes and 4° C. for 7 minutes. A solution of equimolar amount of 40 mM dNTP and Klenow fragment (exo+) (2 unit/ml, For Sequencing, TAKARA) were added thereto and incubated at 37° C. for 30 minutes. Equimolar amount of 10 M urea BPB dye solution was added and kept at 75° C. for 5 minutes and electrophoresed with 20% polyacrylamide-7M urea gel. Products were analyzed by using Phosphoroimager plate. Result is shown in FIG. 12.

Example 11

Transcription by T7 RNA Polymerase

A solution containing template DNA 1 mM, in which promoter region has duplicated strands, T7 RNA polymerase 2.5 units, 2mM rNTP, and [α-$^{32}$P]rATP 0.1 m Ci/ml [40 mM Tris-HCl (pH 8.0), 8 mM MgCl$^2$, 2 mM spermidine, 5 mM DTT, 0.01% Triton X-100, 10 mM rGMP] were prepared and incubated for 3 hours. 10 M urea dye was added and kept at 75° C. for 3 minutes to terminate the reaction. The product RNA (16-mer) in this solution was purified by using electrophoresis with 20% polyacrylamide gel. RNA was digested by 0.75 units RNase T2. Ratio of each nucleotide was determined by 2-dimenstion TLC (cellulose resin). In FIG. 13, result of development of TLC is shown. Ratio of each nucleotide is shown in Table 2 hereinbefore.

Example 12

Synthesis of Primer and Template Containing Base X2

Primer and template were synthesized conventionally by using DNA/RNA synthesizer Type 392, The Perkin-Elmer, Applied Biosystems Div., and cyanoethylamidide reagents of dA, dC, dG and dT, which were distributed by The Perkin-Elmer, and dx2 of cyanoethylamidite reagent prepared according to the method in example 1.

Proviso that in a synthesis of oligomer containing dx2, removal of protective group for 2-amino group of dx2, i.e. isobutyryl group, could not completely be performed, under the usual basic condition after synthesis of oligomer (conc. ammonia at 55° C. for 10 hours), consequently, treatment for removal of the protective group was performed under the condition at 80° C. with conc. ammonia for 10 hours.

Industrial Applicability

The present invention indicates that selective base pair formation, which could never be achieved by the heretofore reported artificial base pair, can be realized by utilizing steric hindrance and electrostatic repulsion as well as stacking action. By utilizing the method of the present invention, artificial nucleic acid base pair of the present invention can be applied on replication and transcription of nucleic acid, and protein synthetic system or functional nucleic acid. For example, by using artificial base pair of the present invention, in vitro selection method used by the natural base of 4 types can be performed by 6 types of bases. Creation of nucleic acid molecules having new function which can not be realized by 4 natural bases. Further, novel base pair of the present invention may be utilized for treatment of hereditary diseases caused by replacement of one or more bases to the other bases.

---

What is claimed is:

1. A method for forming a selective base pair, the method comprising the step of contacting (i) a nucleic acid having, as a base, 2-aminopurine, which is substituted at position-6 by a di(lower alkyl)amino group or a five or six membered aromatic heterocyclic group having 1 or 2 heteroatoms selected from N, O, or S, and (ii) with a nucleic acid having 2-oxo or 2-hydroxy pyridine as a base.

2. The method according to claim 1 wherein five membered aromatic heterocyclic group is thiophene or the di(lower alkyl)amino group is dimethylamino.

3. The method according to claim 1 or claim 2 wherein the base pair is a base pair which can be recognized by a polymerase.

4. The method according to claim 3 wherein the polymerase is DNA polymerase or RNA polymerase.

* * * * *